US010352926B2

(12) United States Patent
Coy

(10) Patent No.: US 10,352,926 B2
(45) Date of Patent: Jul. 16, 2019

(54) AUTOMATABLE METHOD FOR THE IDENTIFICATION, QUANTIFICATION AND DISCRIMINATION OF SPECIFIC SIGNALS IN RELATION TO NON-SPECIFIC SIGNALS IN DETECTION METHODS BY MEANS OF A DETECTOR

(71) Applicant: Johannes C Coy, Hainburg (DE)

(72) Inventor: Johannes C Coy, Hainburg (DE)

(73) Assignee: ZYAGNUM AG, Pfungstadt (DE)

( * ) Notice: Subject to any disclaimer, the term of this patent is extended or adjusted under 35 U.S.C. 154(b) by 330 days.

(21) Appl. No.: 14/785,434

(22) PCT Filed: Apr. 17, 2014

(86) PCT No.: PCT/DE2014/000214
§ 371 (c)(1),
(2) Date: Oct. 19, 2015

(87) PCT Pub. No.: WO2014/169896
PCT Pub. Date: Oct. 23, 2014

(65) Prior Publication Data
US 2016/0084828 A1 Mar. 24, 2016

(30) Foreign Application Priority Data
Apr. 19, 2013 (DE) .................. 10 2013 006 714

(51) Int. Cl.
*G01N 33/52* (2006.01)
*G01N 33/53* (2006.01)
*G01N 33/49* (2006.01)
*G01N 33/50* (2006.01)

(52) U.S. Cl.
CPC ...... *G01N 33/5306* (2013.01); *G01N 33/4915* (2013.01); *G01N 33/5094* (2013.01); *G01N 33/52* (2013.01)

(58) Field of Classification Search
CPC .......... G01N 33/5306; G01N 33/5094; G01N 33/52; G01N 33/4915
See application file for complete search history.

(56) References Cited

U.S. PATENT DOCUMENTS 9,320,723 B2 * 4/2016 Phipps ................. A61K 31/519
2012/0015001 A1 1/2012 Phipps et al.

OTHER PUBLICATIONS

Stjernschantz et al. Localization of prostanoid receptors and cyclo-oxygenase enzymes in Guinea Pig and human cochlea. Hearing Research 197: 65-73 (2004).*

(Continued)

*Primary Examiner* — Gailene Gabel
(74) *Attorney, Agent, or Firm* — Ballard Spahr LLP

(57) ABSTRACT

The invention relates to an automatable method for the identification, quantification and discrimination of specific signals in relation to non-specific signals in detection methods by means of a detector emitting or generating signals, in which at least one control approach is carried out in parallel to the actual test approach, which contains all the components of the actual test approach but in which the binding domain(s) of the detector is/are blocked. The analytical measurements of the signals of the control approach and of the actual test approach are compared with each other and the signal of the specifically bound detector in the test approach is calculated therefrom.

17 Claims, 12 Drawing Sheets

(56) References Cited

OTHER PUBLICATIONS

Hahn et al. (Immunolabelling of Atrazine Residues in Soil Z. Pflanzenernahr. Bodenk. 155 (203-208 (English, 1992) IDS.*
Hahn, et al., (1992) "Immunolabelling of Atrazine Residues in Soil", Journal of Plant Nutrition and Soil Science, vol. 155. No. 3, (pp. 203-208).
Ohta, et al., (2004) "Oxygen-Sensing Mechanism of HemAT from Bacillus subtilis: A Resonance Raman Spectroscopic Study", J. Am. Chem. Soc., vol. 126, (pp. 15000-15001).
Spence, et al., (2004) "Development of a Functionalized Xenon Biosensor", J. Am. Chem. Soc., vol. 126, (34 pages).
Stjernschantz, et al., (2004) "Localization of prostanoid receptors and cyclooxygenase enzymes in Guinea pig and human cochlea", Hearing Research, vol. 197, (pp. 65-73).
Wang, et al., (2005) "Electrostatic Orientation of Enzymes on Surfaces for Ligand Screening Probed by Force Spectroscopy", Langmuir, vol. 22, (pp. 887-892).
International Search Report issued by the International Searching Authority dated Oct. 10, 2014 for international application PCT/DE2014/000214, filed on Apr. 17, 2014 and published as WO 2014169896 on Oct. 23, 2014 (Applicant/Inventor—Johannes F. Coy) (3 pages—English Translation).
International Preliminary Report on Patentability issued by the International Searching Authority dated Oct. 20, 2015 for international application PCT/DE2014/000214, filed on Apr. 17, 2014 and published as WO 2014169896 on Oct. 23, 2014 (Applicant/Inventor—Johannes F. Coy) (8 pages—English Translation).

* cited by examiner

Fig. 2
a)
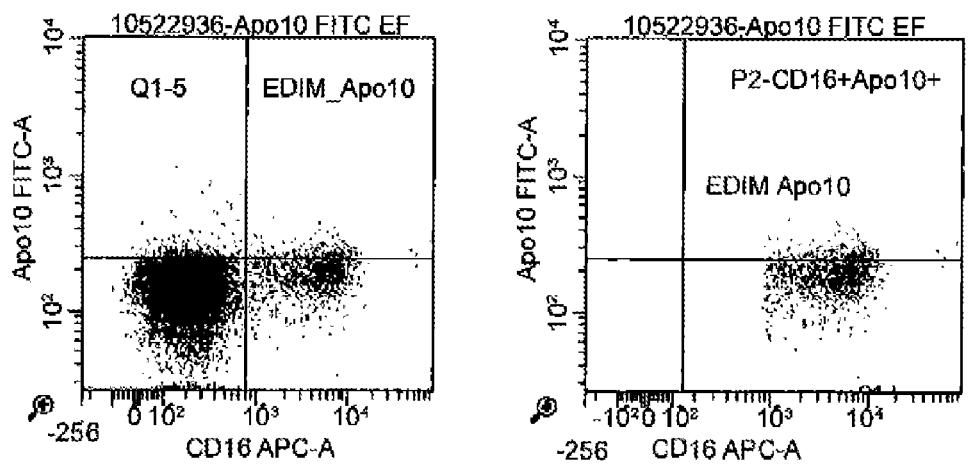
b)
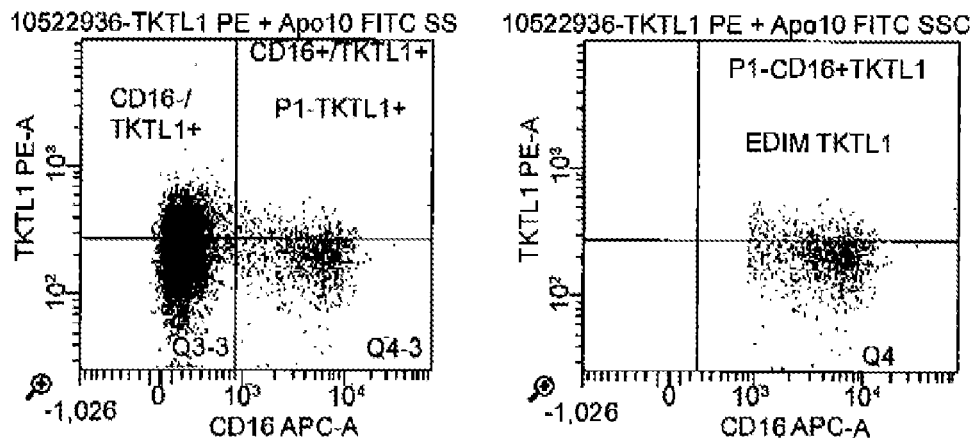

Fig. 3
a)
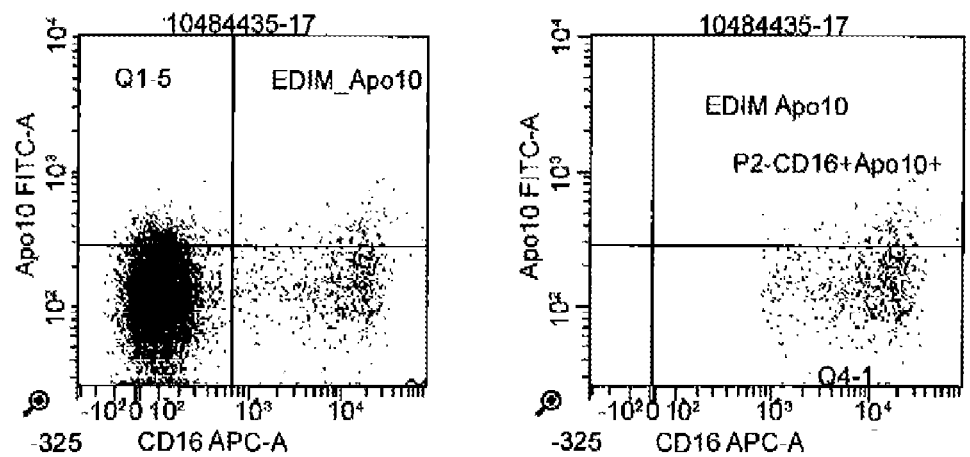
b)
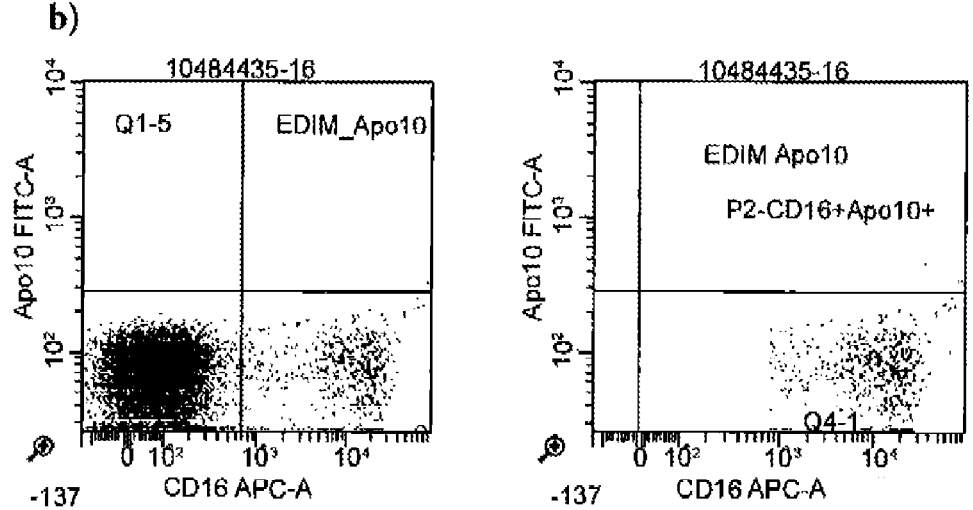

Fig. 5
a)
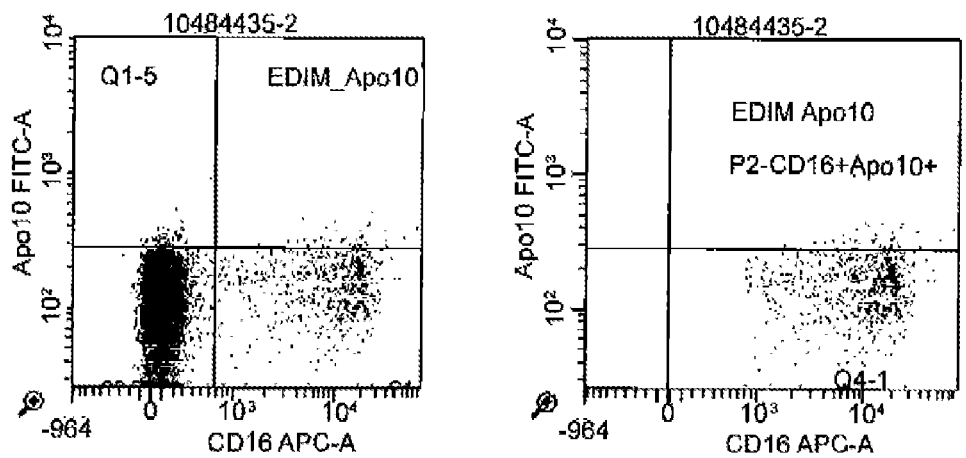
b)
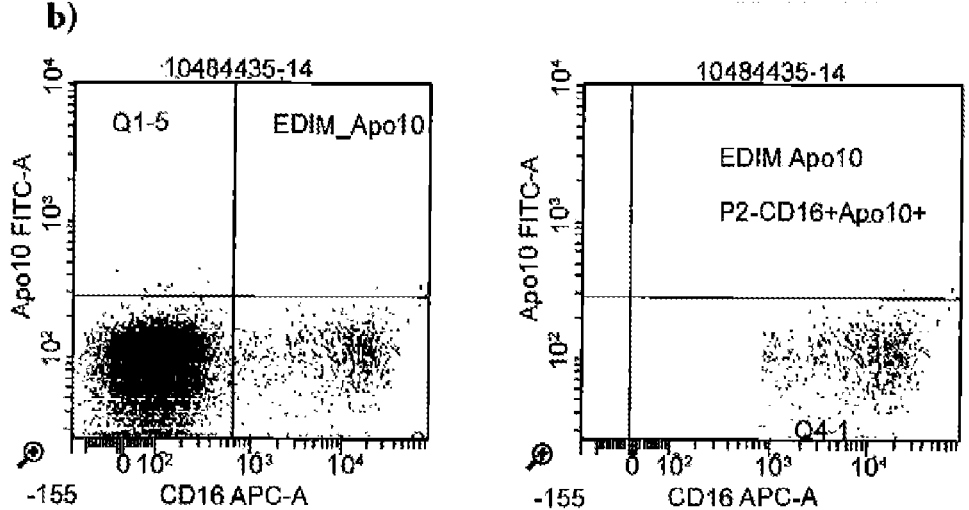

AUTOMATABLE METHOD FOR THE IDENTIFICATION, QUANTIFICATION AND DISCRIMINATION OF SPECIFIC SIGNALS IN RELATION TO NON-SPECIFIC SIGNALS IN DETECTION METHODS BY MEANS OF A DETECTOR

CROSS REFERENCE TO RELATED APPLICATIONS

This application is a national phase filing of International Patent Application No. PCT/DE2014/000214, filed Apr. 17, 2014, which claims priority to German Application No. 10 2013 006 714.6, filed on Apr. 19, 2013, both of which are herein incorporated by reference in their entireties.

BRIEF DESCRIPTION OF THE DRAWINGS

FIG. 2: Cutoff determination on blood sample. a) Antibody Apo10 (FITC) EDIM staining b) Antibody TKTL1 (PE) EDIM staining.

FIG. 3: Relationship between measurement and FMO control with blood sample. a) Antibody Apo10 (FITC) single staining. b) FMO control (without FITC antibody)

FIG. 5: Parallel measurement with unblocked and blocked Apo10 antibody. a) Control preparation with 10-fold excess of blocker peptide. b) Control preparation with 500-fold excess of blocker peptide.

Figure 1:
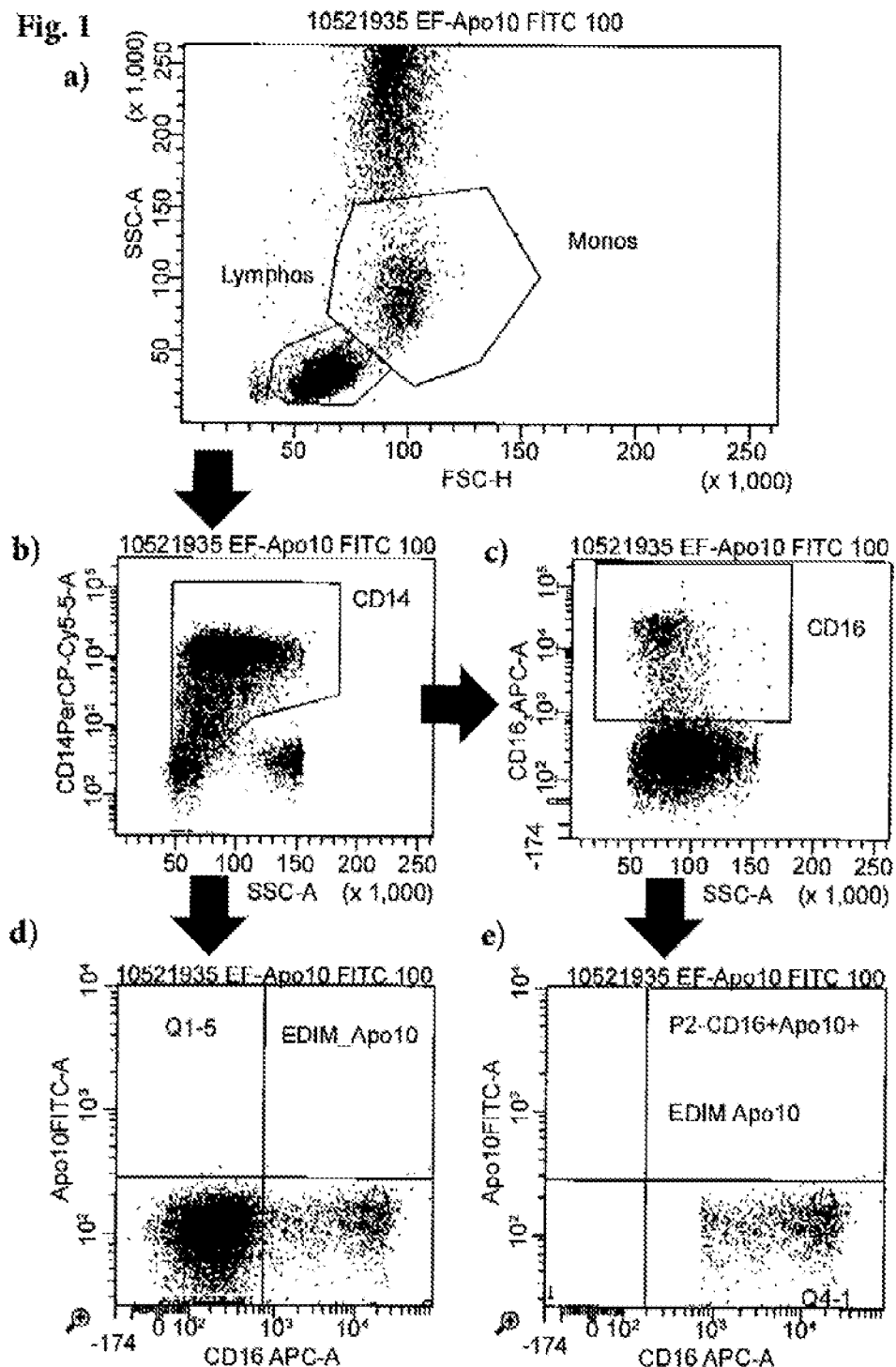
FIG. 1: "Gating strategy" for identification of the macrophages. a) Identification of monocytes ("monos"), through plotting of all leukocytes identified through granularity (SSC-A) and size (FSC-H). b) CD14 positive monocytes. A region (CD14) is positioned. c) CD14 positive cells are further tested for the presence of CD16. A region (CD16) is positioned. d) CD14 monocytes are further tested for the intracellular presence of the Apo10 antibody. e) CD14 and CD16 positive monocytes, Apo10 presence analysis.

The invention relates to a method for the identification, quantification and discrimination of specific signals in relation to non-specific signals ("background signals") in a detection method which is performed on (previously obtained) sample material with use of at least one detector for the discovery and identification (for the detection) of certain target structures, wherein the detector gives out (emits) or generates (e.g. via enzymatic reactions) signals for its detection (i.e. for the detection of the detector) and these signals enable a quantification of the detector, and wherein the specific signals are those signals which the detector gives out (emits) or generates as a result of discovery and identification of the target structure. The detection of diseases or other undesired conditions can be effected through the detection of structures which are specific for the disease or the undesired condition, e.g. as a cause or as an epiphenomenon.

Methods for the detection (discovery and identification) of such structures are often based on the interaction of the structure to be detected with a detector. A detector can for example be an antibody which recognizes an epitope of a protein, or also be an inorganically prepared detector substance which interacts specifically by the lock and key principle with the structure to be detected and thereby makes this detectable.

A decisive factor for the quality of such detection methods is the specificity with which the structure is recognized by the detector. The higher the specificity is, the better it is possible to discriminate between positive and negative test result with the test method.

Every interaction between detector and structure to be detected is characterized by a certain degree of specificity. The higher the specificity of this interaction is, the lower the rate of non-specific detection. However, even if the specificity is very high, non-specific interactions between detector and structure which lead to false positive test results still occur. This non-specific interaction can derive from the part of the detector which interacts directly with the structure, or else be caused by components of the detector which do not interact directly with the structure.

In test methods in which for example a monoclonal antibody is used for the detection of a certain epitope of a certain protein on or in a cell (e.g. tumor cell), the overall result is made up of the specific signal, which results through the specific binding of the variable region of the antibody with the epitope of the protein to be detected, and non-specific signals. The non-specific signals result for example from interactions of the variable region of the antibody with similar epitopes of other proteins or from interactions of the constant region of the antibody with structures of the cell, e.g. with receptors.

If fluorescent dyes are used for the labeling and visualization of the detector, there is the problem that many cells display an intrinsic fluorescence which can moreover be different depending on the wavelength of the excitant light. This intrinsic fluorescence of the cells also falsifies the detected overall signal.

A further cause of non-specific signals consists in the non-specific binding (adhesivity) of antibodies to other cell structures or—in the case of intracellular labeling—in incomplete washing of unbound antibodies out of the cytoplasm.

In order to determine the magnitude of the non-specific binding and other non-specific signals, controls must always be performed.

One form of determination of non-specific signals consists in performing a parallel test procedure without addition of that antibody which recognizes the target antigen (the target structure), the so-called FMO (fluorescence minus one) control.

With FMO control, those non-specific signals which are created by the intrinsic fluorescence of the cell and/or by undesired fluorescence (undesired side-emissions) of the dyes used in the target channel (i.e. in the detection channel for the wavelengths of the light which is emitted by the detection antibody bound to the target epitope or to the target structure are captured.

Such FMO controls are often used for non-adhesive cell types such as for example T cells. It is thereby possible to determine, in the range of the emitted light of that fluorescent dye which is used for the detection of the target antigen, the fraction of the light intensity which is/would also be present in the absence of the detection antibody.

Another form of determination of non-specific signals in the case of detection methods by means of detection antibodies consists in performing a so-called isotype control. For this, the relevant detection method is performed in a parallel control preparation with an isotype of the detection antibody, i.e. with an antibody of the same subtype as the specific detection antibody, but directed against an antigen or epitope which does not occur in the organism which or the cells whereof are studied in the detection method.

A signal which is created by addition of the isotype control antibody stands for a non-specific signal which is generated solely as a result of the "adhesion" of the antibody to cell structures.

The isotype control is in particular always performed when the cells to be tested (which are analyzed as regards the target antigen) are so-called sticky cells such as for example monocytes, dendritic cells, or B cells.

However, both the FMO control and also the isotype control each display only a part of the overall non-specific signal. Simultaneous performance of FMO control and isotype control in the same sample preparation is not possible, and hence nor is any precise determination of all non-specific binding.

In the detection method for intracellular structures using detection antibodies or other detectors, which bind and hence label intracellularly, further non-specific binding occurs, which is still more markedly difficult to determine than in the detection of structures on the surface of cells.

This problem already occurs in the detection of a single intracellular structure and becomes still greater if for example two intracellular structures are to be detected at the same time.

In these methods described as "intracellular staining", holes are generated in the cell membrane by means of a permeabilization buffer, through which the labeled detectors, for example detection antibodies, can pass into the cell. The permeabilization parameters, i.e. the duration of the presence of the holes in the cell membrane and the size of these holes in the cell membrane, must be selected very precisely and in a strictly limited manner in order to avoid lethal damage to the cell, for example through outflow of cytoplasm fluid with important cell components, in order at the same time however to be able to introduce sufficient antibody into the cell and also to be able to wash out unbound antibody out of the cell again after sufficient binding time.

In the case of fluorescence labeled detectors, in particular fluorescence labeled detection antibodies, the analysis of such staining is usually performed by flow cytometry or fluorescence microscopy. In these, the fluorescence and hence the presence of the antibody or detector is determined, irrespective of whether or not the antibody/detector has bound to its target structure (the epitope). In other words, the mere presence of the detector/antibody, irrespective of its binding to the target structure, is assessed via its emitted fluorescence as positive signal. There is no discrimination between detectors/antibodies which have bound the target structure and those which are present free in the cytoplasm or have bound non-specifically. Unbound or non-specifically bound detectors/antibodies contribute substantially to the magnitude of the non-specific signals, since in the case of intracellular staining (in contrast to staining of structures on cell surfaces or tissue sections) efficient washing in order to break even weak non-specific binding again and in order largely to wash unbound detector/antibody out of the cell is not possible.

Because of all this, the detected fluorescence signal of an intracellular detector/antibody is always a mixture of specific signals and non-specific signals. How great the proportion of non-specific signals is here cannot at present be quantified since it is not possible to discriminate between specific and non-specific signals.

The purpose of the present invention is to improve detection methods which are based on the interaction between detector and target structure, to the effect that the specific interactions between detector and target structure are more precisely determinable since the specific positive signals (test results) can more simply and more reliably be discriminated from non-specific signals (test results).

One solution of this problem consists in the provision of a method of the nature initially mentioned which is characterized in that (i) at least one actual test preparation and at least one control preparation are provided, which are handled in parallel, that (ii) the control preparation contains the same components in the same quantities as the actual test preparation handled in parallel and differs from this actual test preparation (preferably solely) in that the binding domain(s) of the detector or the detectors is or are blocked, preferably by a substance (a material, an agent) which is similar to the target structure and that (iii) the totality (or sum) of the measured signals in the control preparation is subtracted from the totality (or sum) of the measured signals in the actual test preparation, wherein the difference represents the specific signal of the detector/the detectors for the target structure(s) to be detected (in other words, the specific signal of the detector is calculated by a comparative measurement between blocked and unblocked detector).

In other words, the solution of this problem consists in (i) performing a parallel experiment, in which before its use the detector is blocked with the structure to be recognized and (ii) comparing the test result which is generated with the blocked detector (i.e. the "control value") with the test result which is generated with the unblocked detector (i.e. with the "test value"), and (iii) in that the difference between the two, i.e. test value minus control value, gives the value which stands for the specific binding of the detector to the target structure or to the substrate to be recognized.

Possible detectors are in particular antibodies, preferably monoclonal antibodies.

If a monoclonal antibody is used as detector, for its use in the control preparation, this "detection antibody" can be blocked at its binding domain with a peptide which corresponds to its target epitope, so that it can no longer bind the target epitope in the sample material. In other words: in the case of detection antibodies, their particular binding domains can be saturated with a "blocker peptide" such that the target epitope (in the sample of the control preparation) can no longer be bound and consequently can no longer be detected.

Especially suitable as such a "blocker peptide" is a peptide which has the amino acid sequence of the target structure, i.e. here the target epitope (i.e. completely or almost completely includes this amino acid sequence or consists thereof).

Also possible as "blocker peptide" are (i) peptides or protein fragments which have the target epitope (the amino acid sequence of the target structure) (i.e. consist thereof or include it), or (ii) whole proteins which have (include) the target epitope (the amino acid sequence of the target structure), or (iii) one or more peptide competitors which is/are similar in function and action to the peptide that have the amino acid sequence of the target epitope (i.e. consist thereof or include it), and which bind to the binding domain(s) of the "detection antibody/antibodies", or else (iv) a combination of one or more peptide competitors and/or protein fragment(s) and/or protein(s), wherein each peptide competitor is similar in function and action to the peptide that has the amino acid sequence of the target structure, and each protein fragment or protein competitor includes the target structure.

In the context of the present invention, the following terms have the following meaning:
Detection=discovery/recognition and display
Binding domain=region on the detector (e.g. the antibody) in which the target structure (e.g. the certain epitope of the protein to be detected) is bound.
Detector=material/substance/agent which specifically recognizes a target structure and interacts (preferably binds) with this target structure at its binding domain.
Detection antibody=antibody, preferably monoclonal antibody, which is used as detector for the discovery/WO recognition and binding to the target structure (here in particular a certain epitope of a certain protein).
Blocker peptide=peptide which blocks the binding domain of the detection antibody so that the target epitope can no longer bind.
Specific signal=signal which the detector or label coupled onto this detector gives out (emits) when (as soon as) it has discovered its target structure and coupled/bound thereto.
Test preparation (synonym: "actual test preparation"= (sample) preparation with "search- and detection-capable" detector, the binding domain whereof for the target structure has not been (previously) blocked.
Control preparation=(sample) preparation with the same components in the same quantities as the (actual) test preparation, wherein however the detector on addition to the preparation is blocked at its binding domains for the target structure, i.e. has previously been specifically blocked at this binding domain.

With the method according to the invention, it is possible in an extremely simple manner specifically to distinguish between specific and non-specific interactions (binding) of the detector, and to determine which of the detector signals detected are specific and which are non-specific. This is associated with a significant heightening of the detection method concerned, connected with considerably higher certainty of the diagnosis.

In the case of a detection antibody, with the method according to the invention in particular that non-specific binding is also captured which is caused by the constant section of the detection antibody or by a secondary antibody, and/or which derive from dyes or enzymes which are coupled onto the antibodies.

The magnitude of the non-specific binding can also be different inter-individual (i.e. within one organism), and non-specific signals based on such inter-individual differences can also be recognized and taken into account with the method according to the invention. For example, the increased concentration of a protein XY and non-specific binding of the antibody to this protein associated therewith can lead to an increase in the non-specific signal. If the concentration of this protein XY is subject to inter-individual fluctuations, then during use of the conventional test methods with control preparations, in which the samples originate from a healthy organism/individual B, this can lead to false results, because an increased signal in the test preparation with samples from individual A in comparison with the control preparation with samples from individual B is assessed as specific signal and is not attributed to an increased non-specific signal which has come about through the non-specific binding to the protein XY present in higher concentration. For example, immunological reactions such as hay fever or an influenza disease can result in the content of certain immune cells within the blood increasing, so that the detection antibody/antibodies come into contact with such sticky cells (e.g. macro-phages) to a greater extent and enter into non-specific bonding with these, as a result of which the proportion of non-specific signals increases in the individual.

With the method according to the invention, these non-specific signals are also captured in the parallel experiments with block detection antibodies (the "control preparations"). By subtraction of the overall measured value of the non-specific signals of these control preparations from the overall measured value of the signals of the actual test preparations, the measured value for the specific signals is calculated and the magnitude of the specific binding individually determined. Particularly in the case of weak specific signals or rarely occurring cell types (e.g. tumor cells), the specificity of the relevant detection method can thus be markedly increased.

Preferred embodiments of the method according to the invention consist in that the detection test is a flow cytometry test method and is performed by flow cytometry, or that the detection test is a fluorescence microscopy test method and is performed by fluorescence microscopy, or that the detection method is a combination of flow cytometry and fluorescence microscopy test methods and is performed by flow cytometry and fluorescence microscopy.

With the introduction of this control measurement into detection methods, in particular into the known immuno-histochemical and immunocytological detection methods with fluorescence microscopy and/or flow cytometry as the analytical method, these can be performed more reliably and securely. The assessment of the test results is considerably simplified because the two measurements of (actual) test preparation and control preparation can be directly compared with one another or subtracted from one another. In addition, the sensitivity of the test concerned can be enormously increased, since through the measurement of the background signals (the non-specific binding) in the control preparation and subtraction of these measured values from the measured values with the actual test preparation the specific signal can be calculated and thus in practice the ratio of signal to background is improved.

Thus for example those cells which only occur at low cell count, e.g. circulating tumor cells or especially rare immune cells, can also be efficiently and simply determined in the blood. Monocytes or macrophages can also be detected and analyzed markedly better, since the proportion of the non-specific signals can be determined and subtracted from the overall signal.

In the case of samples which derive from (presumably) diseased donor organisms (patients), and in particular when it can already at an early stage be presumed that the magnitude of the non-specific signals is quite high, and/or the non-specific signals fluctuate between individuals and/or have been/are influenced by changes in the donor organism, in particular in its immune system (such as for example as a result of colds, hay fever or use of cortisone), the use of the method according to the invention offers major advantages: since these non-specific signals are captured and measured separately, and the measured value for the/each specific signal can be calculated with high accuracy on the basis of these measured values, the results of the detection method are more accurate, secure and reliable, and likewise the diagnoses based thereon.

In the case of immunocytological detection methods with intracellular staining, the following situation results with the detection method according to the invention: After the temporary generation of holes in the cell membrane, the introduction of the peptide-blocked fluorescence-stained antibody into the cell, the subsequent washing and closing of the pores, a certain proportion of the fluorescence labeled detection antibody remains in the cell (some unbound but not washed out and some non-specifically bound). Its emitted signals indicate the magnitude of the non-specific binding.

In parallel to this, the unblocked fluorescence-stained antibody is used in an otherwise identical manner in an otherwise identical experiment. Through the specific binding of the antibody onto the target epitope, a firm bond between antibody and target epitope is created, which is not loosened by washing or diffusion. However, non-specific binding of the antibody to cell structures also occurs here, so that non-specific signals are generated.

However, on the basis of the specific binding of the antibody and the less intense washing out of the cell associated therewith, the overall signal is higher than that in the parallel measurement with blocked antibody. The signal of the parallel measurement in the control preparation with the blocked antibody ("control measurement") is subtracted from the overall signal of the measurement of the test preparation with unblocked antibody ("test preparation"), and only the measured values remaining are to be assessed as specific measurement signals.

In the case of immunohistochemical and immune-cytological detection methods, the following situation results with the detection method according to the invention:

In the immunohistochemical and immunocytological detection methods, according to the invention, in parallel with the actual test preparations, in which the detection antibodies with free, i.e. unoccupied or unblocked, binding domains are used, as a control or control test, a comparative measurement is performed on (at least) one control preparation, which differs from the relevant parallel "actual" test preparation (preferably only) in that the/each detection antibody is coupled or saturated at its binding domain with a peptide or a competitor comparable in its action (i.e. with the same function and action or with similar action), so that a specific binding of the antibody to "its" epitope in/on the target structure (the subject of the test). The measurement of the antibody signals in/on this control preparation and comparison thereof with the measured antibody signals in the actual test preparation enables the determination of the non-specific and the specific signals of the particular test method: the overall signal of the actual test preparation minus (after subtraction of) the non-specific signals in the control preparation yields the value for the specific signal of the target structure which is the subject of the test.

Admittedly it is known that in immunohistological detection methods using antibodies as detectors it is possible to discriminate non-specific signals from specific signals by "blocking" the antibody, e.g. with a peptide, however the immunological test is then not performed with parallel test and control preparations (test preparation with unblocked antibody and control preparation with blocked antibody). Hence no measured value for the non-specific signals is determined, and no difference determination for the calculation of the measured value for the specific signals (specific signal value) is performed. Instead of this, only measurements on test preparations with unblocked antibody are performed, and consequently the results obtained in the form of the measured signals of the antibody always represent the mixture of signals from specifically bound and non-specifically bound antibody.

The method according to the invention can also without difficulty be combined with part-automatic (partly automatic) or fully automatic assessment methods. In the prior art, not only in flow cytometry, but by now also often in immunohistochemistry, the results of detection methods with immunohistochemical staining are digitally captured and assessed. With use of the method according to the invention with parallel determination of the non-specific signal, a direct comparison of the two stainings of actual test preparation and control preparation of the/each actual test preparation is thus also possibly digitally, i.e. the difference value between the results of the/each actual test preparation and that of the/each control preparation can be determined with digital assessment programs, whereby the analysis of histochemical samples overall is further facilitated and accelerated and at the same time is more reliable and more secure.

Preferred embodiments of the method according to the invention therefore also consist in that the detection of the reaction signals in control preparation (RS-C) and actual test preparation (RS-T) and/or the subtraction (RS-T minus RS-C) and difference display is effected partly automatically or fully automatically.

If the detection test is an immunohistochemical test, the test results, i.e. the results of the immunohistochemical staining, are captured and assessed digitally, i.e. the detection of the reaction signals in control preparation (RS-C) and actual test preparation (RS-T) is effected digitally, the subtraction (RS-T minus RS-C) is effected partly automatically or fully automatically, and the difference display is effected digitally.

If the detection test is an immunofluorescence test, the test results, i.e. the immunofluorescence results are captured and assessed digitally, i.e. the detection of the emission signals in control preparation (RS-C) and actual test preparation (RS-T) is effected digitally, the subtraction (RS-T minus RS-C) is effected partly automatically or fully automatically, and the difference display is effected digitally.

The invention is explained in more detail below on the basis of practical examples and diagrams corresponding thereto.

The diagrams show:

FIG. 1: "Gating strategy" for identification of the macrophages.

a) For the identification of the monocytes (here referred to as "monos"), all leukocytes are plotted both in terms of their granularity (SSC-A) and also in terms of their size (FSC-H).

b) Only the cells thus characterized are tested for the presence of the surface marker CD14. These include both the brightest (=highly positive), in the upper, oval cloud of points and the intermediately bright (=normal positive) cells. A region (referred to as 'CD14') is positioned around these for further characterization.

c) This is additionally further tested for the presence of the surface marker CD16. These include both the brightest (=highly positive), in the upper, oval cloud of points and the intermediately bright (=normal positive) cells. A region (referred to as CD16) is likewise positioned around these for further characterization.

d) All cells identified both as 'monos' and also as 'CD14' are further tested for the intracellular presence of the Apo10 antibody—for the purpose of optimizing the subjective cutoff estimation.

e) The cells contained in the region 'monos' and also in 'CD14' which additionally bear the surface marker CD16 count as "genuine macrophages". They are separated by the horizontally lying cutoff, and the cells are thereby identified as "Apo10 positive cells" (CD14 positive, CD16 positive, Apo10 positive).

As the result of the measurement, the 'epitope detection in monocytes/macrophages' (EDIM) value is shown as the relative quantity of CD14+/CD16+ positive macrophages which are Apo10 positive (in comparison to the overall quantity of the CD14/CD16 positive macrophages).

FIG. 2: Cutoff determination on blood sample a) Antibody Apo10 (FITC) EDIM staining The proportion of Apo10 positive macrophages (Apo10 positive, CD14 positive and CD16 positive) in the right-hand picture segment (red signal points), i.e. of the macrophages which give a light signal in the FITC measurement channel, lies at 16.7% above the horizontal cutoff (separation boundary).

In the left-hand picture, the monocytes not further interpreted here can be seen. This applies also for the following diagrams.

b) Antibody TKTL1 (PE) EDIM staining

The proportion of TKTL1 positive macrophages (TKTL1 positive, CD14 positive and CD16 positive) in the right-hand picture segment (red signal points), i.e. of the macrophages which give a light signal in the FITC measurement channel, lies at 17.2% above the horizontal cutoff (separation boundary).

FIG. 3: Relationship between measurement and FMO control with blood sample a) Antibody Apo10 (FITC) single staining The proportion of Apo10 positive macrophages (Apo10 positive, CD14 positive and CD16 positive) in the right-hand picture segment (red signal points), i.e. of the macrophages which give a light signal in the FITC measurement channel, lies at 16.7% above the horizontal cutoff (separation boundary).

b) FMO control (without FITC antibody)

The proportion of positive macrophages in the right-hand picture (labeled in red) lies clearly distanced from the unstained macrophage cloud at only 0.8% above the horizontal cutoff. The cutoff was transferred from the measurement (a) to the FMO control measurement. This also applies for the following FMO control diagrams.

Figure 4:
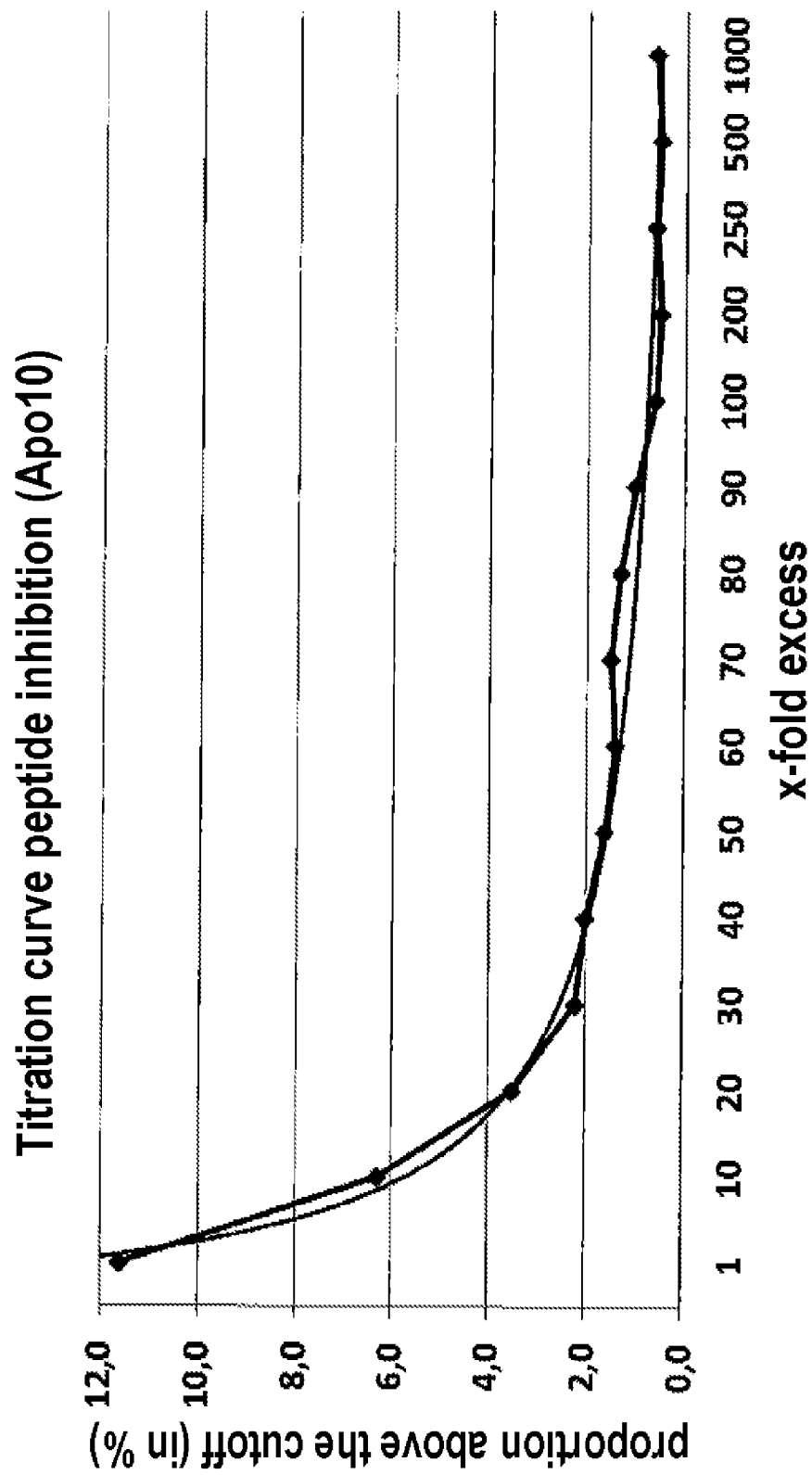
FIG. 4: Titration curve. Staining of patient blood with 1-fold to 1000-fold concentration of the molar excess of peptide to antibody Apo10.

FIG. 4: Titration curve

Staining of patient blood with 1-fold to 1000-fold concentration of the molar excess of peptide to antibody Apo10. The increasing content of peptide excess (molar excess of peptide to antibody) is shown on the x axis, and the relative value of the Apo10 positive macrophages above the cutoff (in %) on the y axis.

FIG. 5: Parallel measurement with unblocked and blocked Apo10 antibody a) Control preparation with 10-fold excess of blocker peptide.

b) Control preparation with 500-fold excess of blocker peptide.

Figure 6:
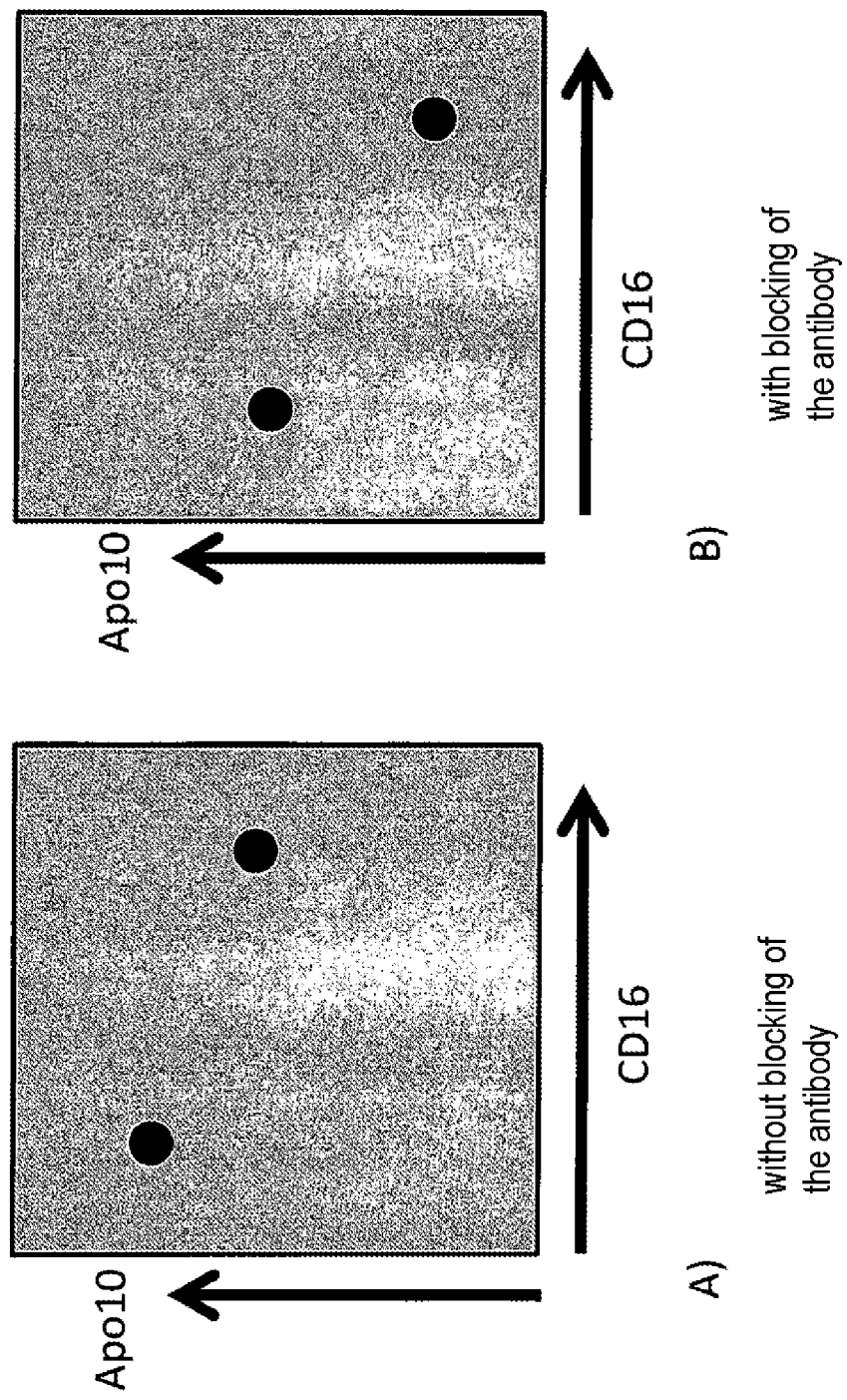
FIG. 6: Schematic diagram of the flow cytometry analysis of two cells with Apo10 (fluorescence) signal of different strength. The X axis shows the CD16 signal; the Y axis shows the Apo10 signal. A) Cells with unblocked Apo10 antibody. B) Cells with blocked Apo10 antibody.

FIG. 6: Schematic diagram of the flow cytometry analysis of two cells with Apo10 (fluorescence) signal of different strength The X axis shows the CD16 signal; the Y axis shows the Apo10 signal.

A) Cells with unblocked Apo10 antibody.

B) Cells with blocked Apo10 antibody.

Figure 7:
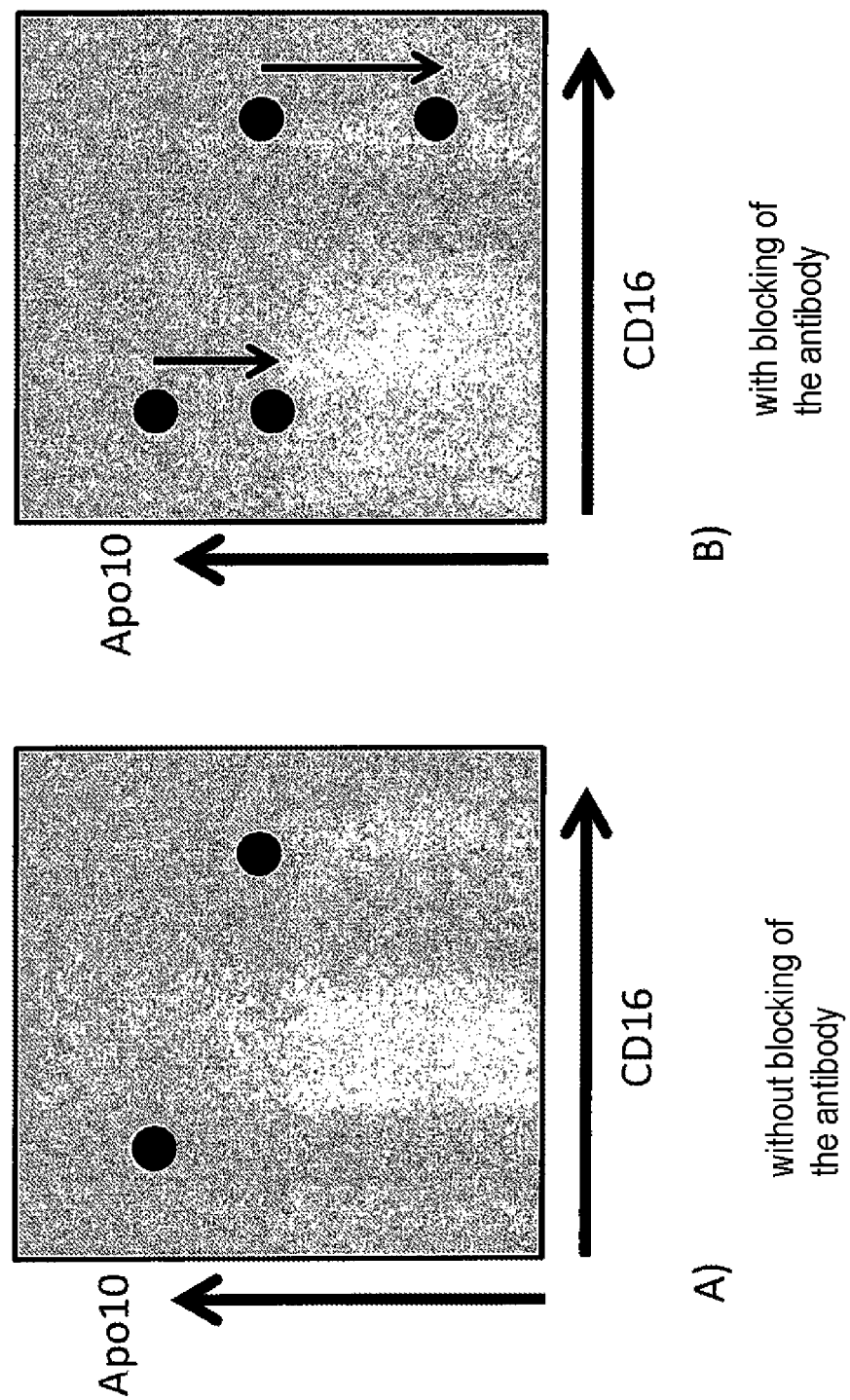
FIG. 7: Schematic diagram of the flow cytometry analysis of two cells with Apo10 (fluorescence) signal of different strength and representation of the magnitude of the reduction in the Apo10 signal. The X axis shows the CD16 signal; the Y axis shows the Apo10 signal. A) Cells with unblocked Apo10 antibody. B) Cells with blocked Apo10 antibody. The length of the arrows (downwards) corresponds to the magnitude of the decrease in the Apo10 signal after blocking of the antibody.

FIG. 7: Schematic diagram of the flow cytometry analysis of two cells with Apo10 (fluorescence) signal of different strength and representation of the magnitude of the reduction in the Apo10 signal The X axis shows the CD16 signal; the Y axis shows the Apo10 signal.

A) Cells with unblocked Apo10 antibody.

B) Cells with blocked Apo10 antibody. The length of the arrows (downwards) corresponds to the magnitude of the decrease in the Apo10 signal after blocking of the antibody.

Figure 8:
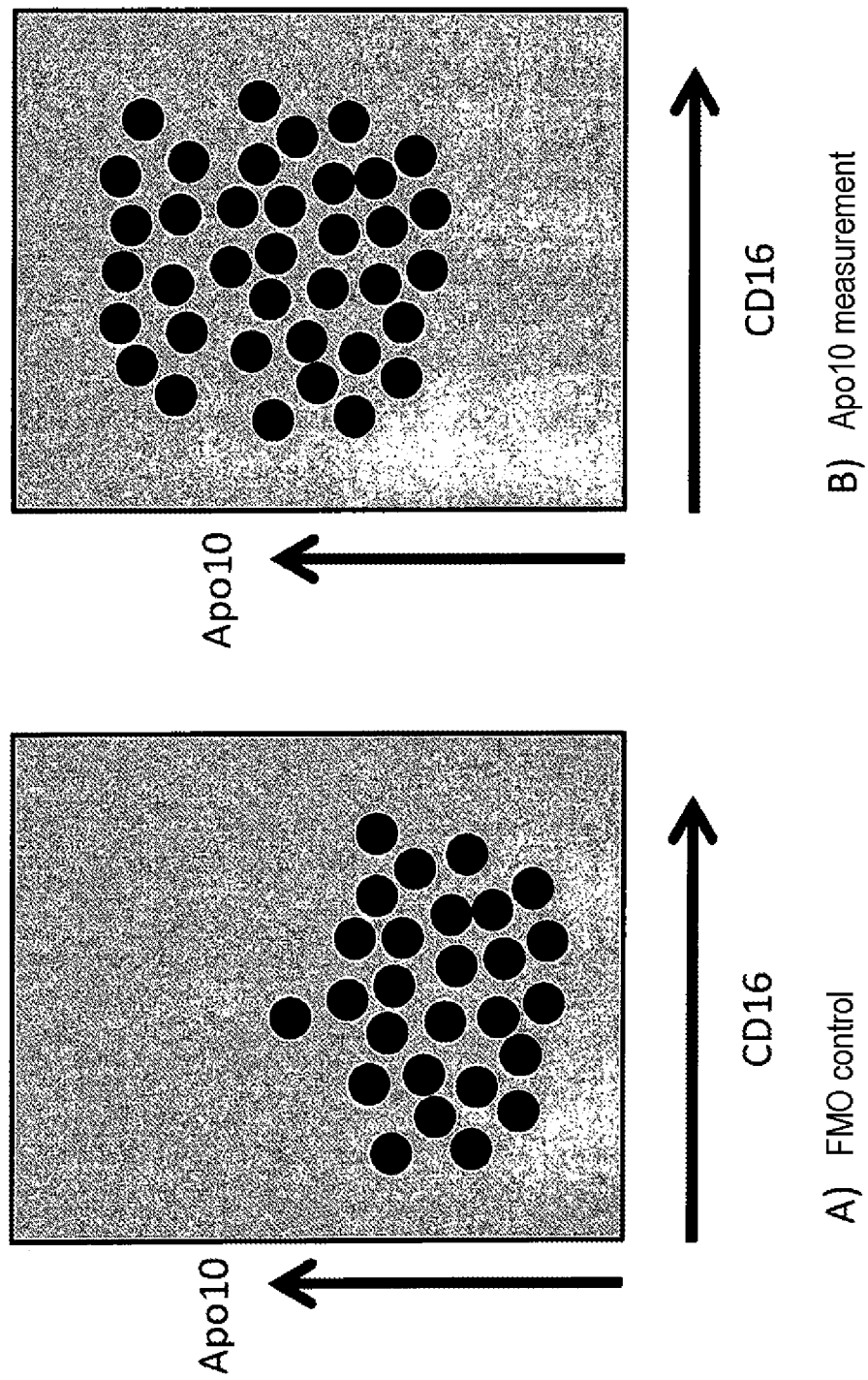
FIG. 8: Schematic diagram analogous to FIG. 6 and FIG. 7 for the analysis of ("actual") test preparation and FMO control. A) Cells of the FMO control (without addition of Apo10 antibody). B) Cells of the ("actual") test preparation after labeling with the fluorescence labeled Apo10 antibody.

FIG. 8: Schematic diagram analogous to FIG. 6 and FIG. 7 for the analysis of ("actual") test preparation and FMO control A) Cells of the FMO control (without addition of Apo10 antibody).

B) Cells of the ("actual") test preparation after incubation and staining (labeling) with the fluorescence labeled Apo10 antibody.

Figure 9:
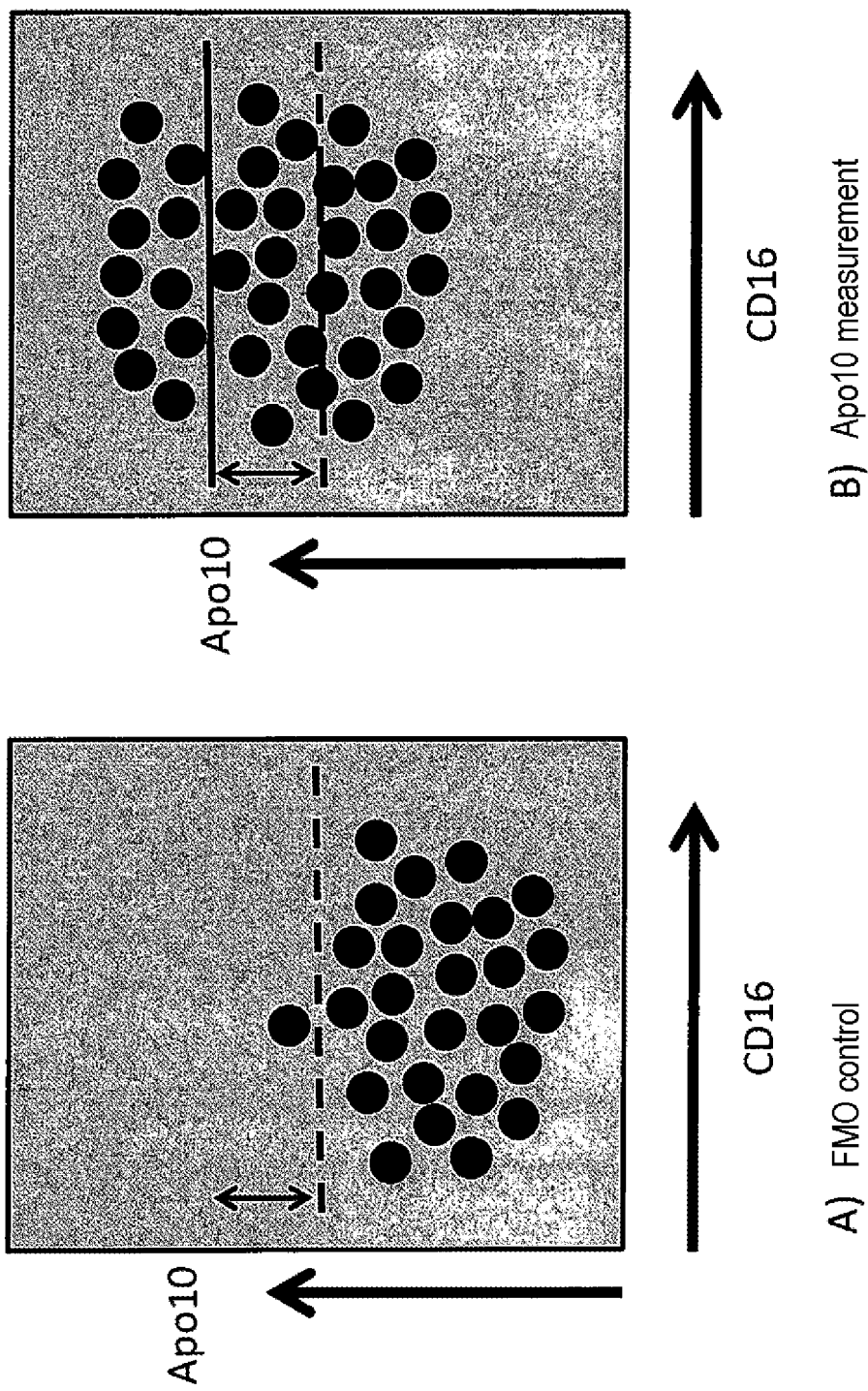
FIG. 9: Diagram of FIG. 8 with cutoff positioned. A) Cells of the FMO control (without addition of Apo10 antibody). B) Cells of the ("actual") test preparation after incubation and staining (labeling) with the fluorescence labeled Apo10 antibody. The dashed line marks the cutoff above the FMO cell cloud.

FIG. 9: Diagram of FIG. 8 with cutoff positioned

A) Cells of the FMO control (without addition of Apo10 antibody).

B) Cells of the ("actual") test preparation after incubation and staining (labeling) with the fluorescence labeled Apo10 antibody. The dashed line marks the cutoff above the FMO cell cloud.

Figure 10:
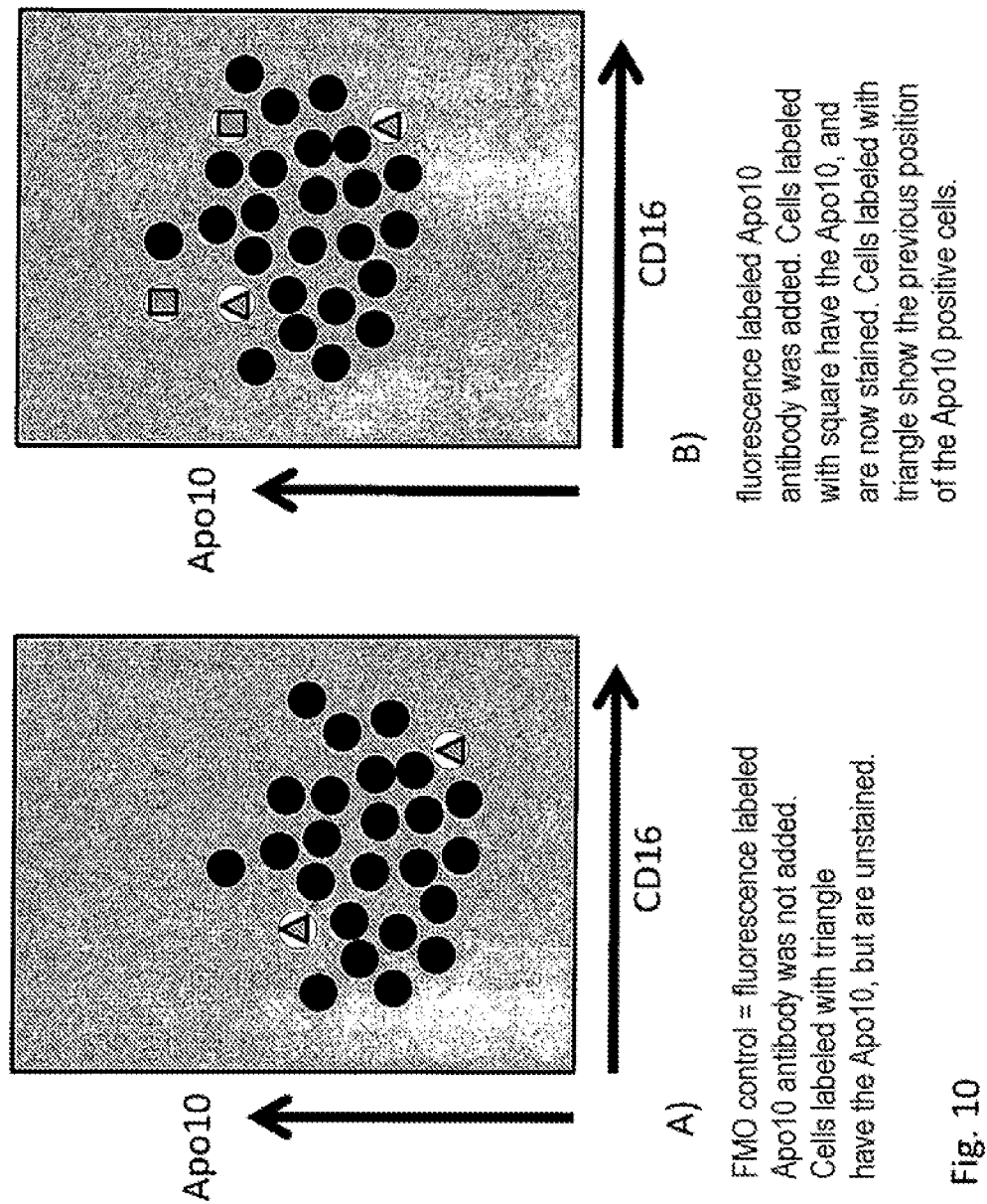
FIG. 10: Schematic diagram of the flow cytometry analysis of cells after incubation with fluorescence labeled Apo10 antibody ("actual" test preparation) and cells of an FMO control Apo10 positive cells (▲). Cells which bear the Apo10 antigen and are labeled with the fluorescence labeled Apo10 antibody and emit corresponding fluorescence signals (■). A) FMO control values (without addition of Apo10 antibody). Unstained Apo10 positive cells (▲). B) Apo10 labeled cells. Stained Apo10 positive cells (■). ▲ are according to FIG. 10 A.

FIG. 10: Schematic diagram of the flow cytometry analysis of cells after incubation with fluorescence labeled Apo10 antibody ("actual" test preparation) and cells of an FMO control Cells which bear the Apo10 antigen are shown as a circle with a triangle inside (▲) Cells which bear the Apo10 antigen and are labeled with the fluorescence labeled Apo10 antibody and emit corresponding fluorescence signals are here each shown as a circle with a square inside (■).

A) Measured values of the FMO control (without addition of Apo10 antibody). Apo10 antigen positive cells (circle with triangle) are present, but are not detected.

B) Cells after incubation and staining (labeling) with the fluorescence labeled Apo10 antibody. Apo10 antigen positive cells are now stained by bound Apo10 antibody (circle with square). The two circles with triangle (▲) shown here indicate the previous position of the two Apo10 antigen-bearing cells according to FIG. 10 A.

Figure 11:
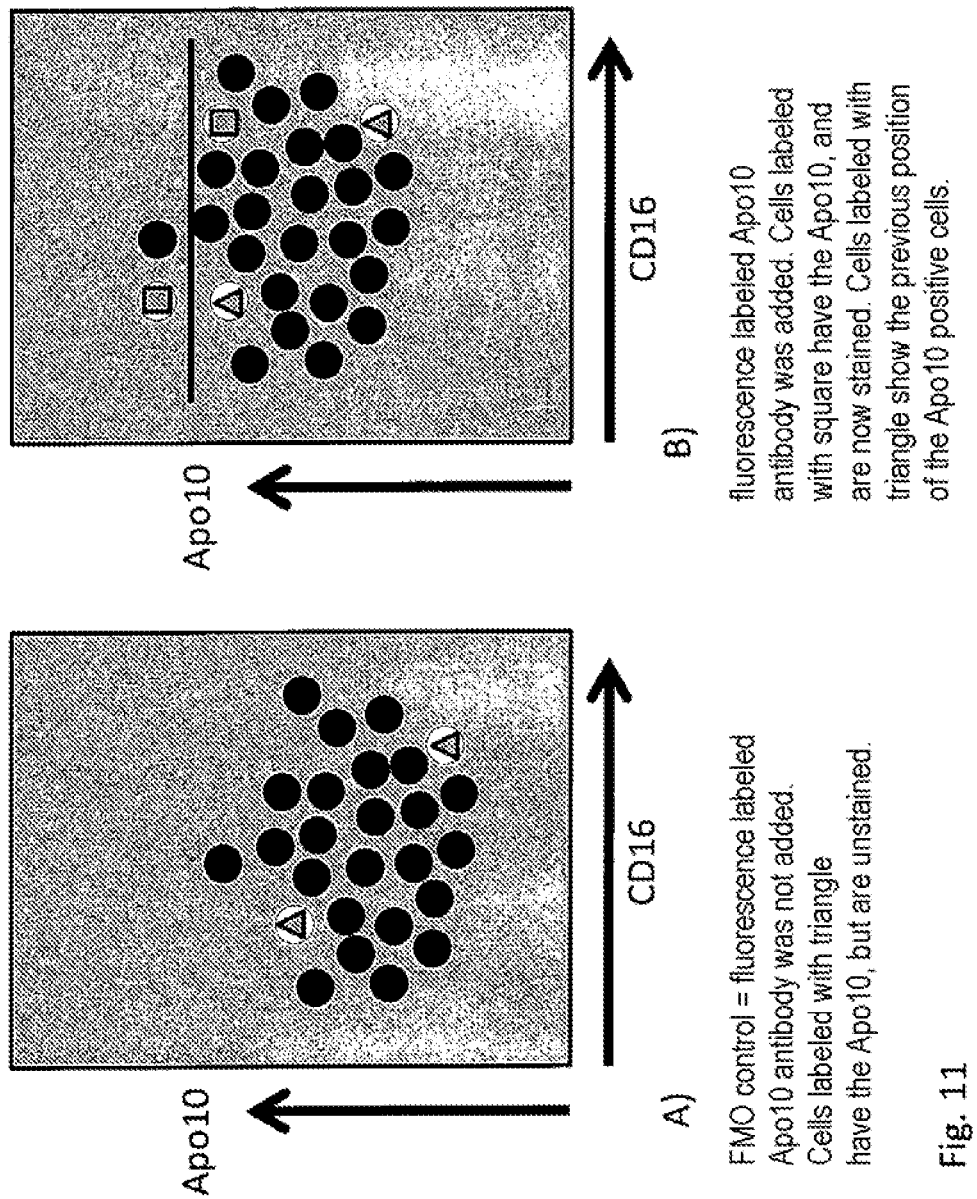
FIG. 11: Diagram according to FIG. 10 with cutoff positioned. A) Cells of the FMO control (without addition of Apo10 antibody). B) Cells of the ("actual") test preparation after labeling with fluorescence labeled Apo10 antibody.

FIG. 11: Diagram according to FIG. 10 with cutoff positioned.

A) Cells of the FMO control (without addition of Apo10 antibody).

B) Cells of the ("actual") test preparation after incubation and staining (labeling) with the fluorescence labeled Apo10 antibody.

Figure 12:
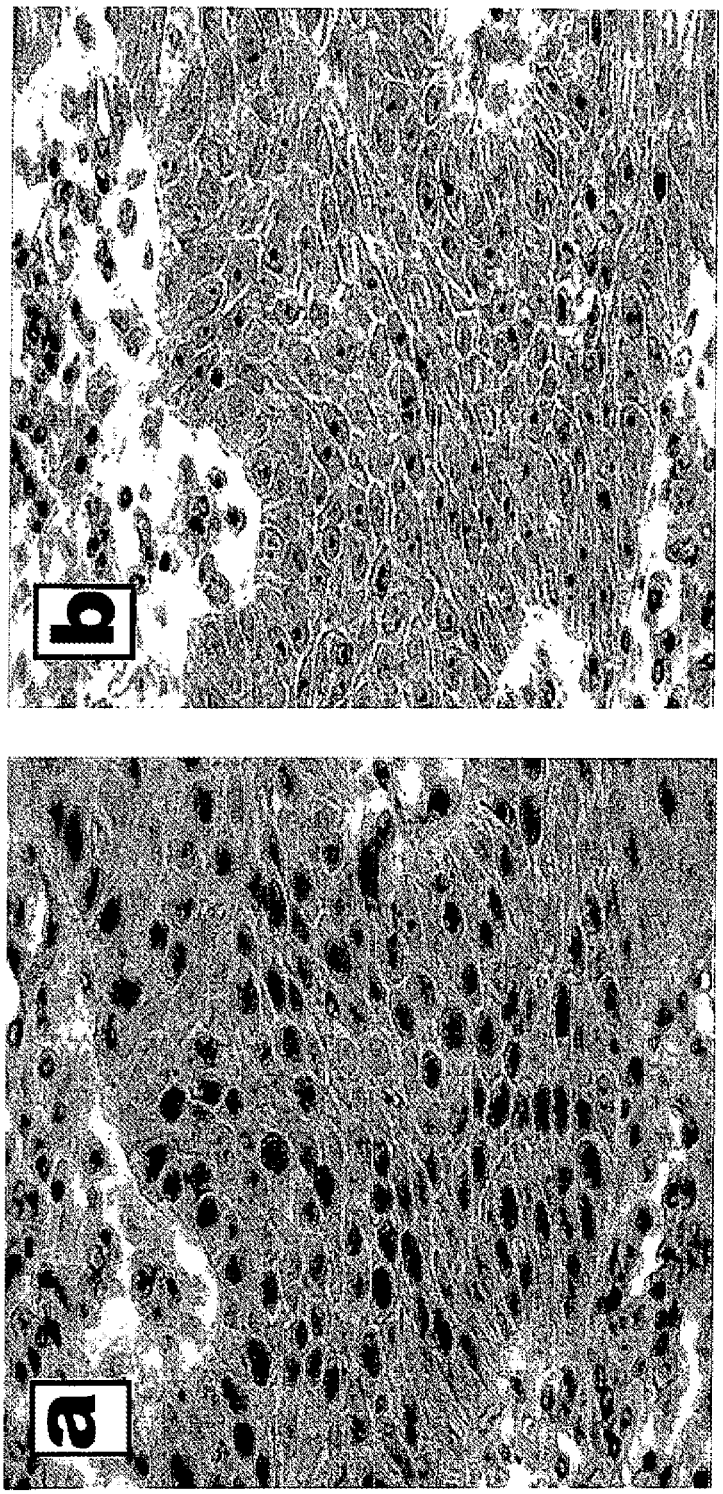
FIG. 12: Tissue sections of oral cavity carcinoma after incubation with the detection antibody. Apo10 for the identification of tumor cells which have an elevated proportion of DNaseX protein with Apo10 epitope in the cell nucleus. a) Staining with unblocked Apo10 antibody. b) Staining with the target epitope/target peptide blocked Apo10 antibody.

FIG. 12: Tissue sections of oral cavity carcinoma after incubation with the detection antibody Apo10 for the identification of tumor cells which have an elevated proportion of DNaseX protein with Apo10 epitope in the cell nucleus
 a) Staining with unblocked Apo10 antibody.
 b) Staining with the target epitope/target peptide blocked Apo10 antibody.

EXAMPLE 1: USE OF THE METHOD ACCORDING TO THE INVENTION ON A BLOOD SAMPLE

For the analysis of a sample, e.g. of a blood sample (from a patient), at least two parallel preparations and parallel measurements are thus necessary: at least one "actual test preparation" and at least one "control preparation".

These two preparations differ only in that in the "control preparation" the binding domain(s) of the detection antibody/antibodies is/are blocked, whereby specific binding is prevented.

From the comparison of the measurement results of the two preparations, the magnitude of the non-specific binding, which arises for example from the constant part of the detection antibody or from a secondary antibody or from dyes or enzymes coupled onto the antibodies, can be determined.

In the case of intracellular staining in immunocytology by means of intracellularly binding detection antibodies, with the method according to the invention the proportion of the antibodies or of the signal deriving therefrom, which admittedly is not bound but also has not been washed out of the cell and hence has remained non-specifically in the cell, can also be determined.

The variability of non-specific binding or of binding which is in fact generated from structures of the antibody independently of the actual binding domains, can also be individually determined with the method according to the invention. Thus for example the magnitude of the binding of the constant part of the detection antibody with certain immune cells which have altered as a result of an immunological reaction in the body can be determined and such false positive signals can also be recognized and eliminated.

Admittedly under some circumstances a higher consumption of reagents and test material is associated with the test method according to the invention since the sample volume (tissue samples, blood) is doubled on account of the parallel control preparation. However, this increased expenditure is more than compensated by extremely specific signals and higher security of the diagnosis and higher sensitivity associated therewith.

EXAMPLE 2: USE OF THE METHOD ACCORDING TO THE INVENTION ON A TISSUE SECTION SAMPLE

For the analysis of a tissue section sample (from a patient), at least two parallel preparations and parallel measurements are necessary: at least one "actual test preparation" and at least one "control preparation".

The handling and treatment of these at least two test preparations is effected as described in example 1.

EXAMPLE 3: DETECTION TEST WITH TWO OR MORE DETECTION ANTIBODIES

The form according to the invention of the parallel testing can of course also be implemented with two or more detection antibodies which are blocked with the respective target peptide sequences (or other target structures). In this case, the signal of the measurement without peptide competition is subtracted from the measurement with the simultaneous competition with several peptides, in order to determine the specific signal which is generated by the binding of the antibody or antibodies with the binding domain.

EXAMPLE 4: USE OF THE METHOD ACCORDING TO THE INVENTION IN FLOW CYTOMETRY

The use of flow cytometry enables a quantitative determination of fluorescence labeled particles, in particular also fluorescence labeled cells (Fluorescence Activated Cell Sorting, "FACS").

The fluorescence labeled cells are passed by means of a liquid flow past one or more lasers, whereby the cells are irradiated with the relevant excitation wavelength(s). As a result of this, the cells emit light of another wavelength. The emitted light is proportional to the quantity of the bound antibody. The data are then passed on to an evaluation program and displayed in diagrams.

Among the most frequent and simplest flow cytometry applications is the analysis of surface structures on individual cells, wherein these surface structures are detected by means of fluorescence labeled antibodies which bind to these structures (so-called "detection antibodies"). As well as protein epitopes, the detectable epitopes of such detection antibodies can also be other structures such as for example sugar structures, fats or modifications of proteins such as phosphate groups.

Another application of FACS is the detection of intracellular molecules such as DNA and RNA, or of intracellular protein epitopes. The specific signal deriving from the target structure is as a rule determined by the comparison with control cells. As a result of this, for example statements can then be made concerning the cell cycle and apoptosis, or certain cell types detected, such as for example normal, healthy cells or tumor cells or malignant tumor cells (cancer cells).

As well as the determination of epitopes on and in cells, it is also possible by means of cell cytometry to determine structures in solutions such as for example cell culture supernatants or serum. For this, beads (or other carriers) are equipped with one or more fluorescence labeled antibodies and added to the sample to be tested, so that the relevant antigen(s) (e.g. interleukins) from the sample bind onto the bead-immobilized antibody.

EXAMPLE 5: USE OF THE METHOD ACCORDING TO THE INVENTION IN FLOW CYTOMETRY WITH THE ANTIBODIES 'APO10' AND 'TKTL1' ON BLOOD SAMPLES

By means of flow cytometry, intracellular structures in immune cells (phagocytizing immune cells such as monocytes/macrophages) are to be detected.

For this, firstly antibodies are selected which specifically label the surface of the immune cells to be tested (extracellular structures) in order to be able to identify these. Secondly, antibodies which detect the intracellular structures in the immune cells are selected. The antibodies "Apo10" and "TKTL1" are directed against intracellular epitopes.

The antibodies are coupled with different fluorescing dyes (fluorochromes) which within the flow cytometry light up (emit) differently after excitation with laser light and can thus be identified. Via the emission, the binding or the presence of the antibody on or in cells can be made visible (monitored).

In order to detect structures internally (intracellularly) in the selected cells, a permeabilization buffer, which generates holes in the cell membrane in order to introduce antibodies into the cells, is used.

In order to determine the proportion of non-specific signals, which in the present case can be particularly high owing to intracellular staining with patient blood with "sticky" monocytes and macrophages, parallel experiments ("control preparations") are performed in which before their use the (detection) antibodies 'Apo10' and/or 'TKTL1' are each saturated in their binding domain with a "blocker peptide", so that they no longer bind their target epitope and consequently can no longer detect.

The test results which are generated with the blocked (detection) antibodies (these "control value") are compared with those test results which are generated with the unblocked antibodies 'Apo10' and/or 'TKTL1' (the "actual test values"). The difference between the two, i.e. (actual) test values minus control values, gives the value which stands for the specific binding of the antibody 'Apo10' or of the antibody 'TKTL1' onto the target structure.

As such a "blocker peptide", here in the example in each case the peptide which was used for the immunization of the antibody-producing cells during the generation of the antibody concerned and the amino acid sequence whereof is consequently identical with or very similar to the amino acid sequence of the target epitope is used.

The implementation of the test is described below:
Material and Methods
Kit: IntraPrep from Beckman Coulter (# A07803);
Antibodies: (except Apo10) from BD Biosciences, Heidelberg
Handling scheme:

| Tube | FITC | PE | PerCP | APC |
| --- | --- | --- | --- | --- |
| 1 (FMO) | | | CD14 (# 345786) | CD16 (# 561304) |
| 2 (EDIM staining) | | | CD14 (# 345786) | CD16 (# 561304) |
| 3 (Peptide blocking) | | | CD14 (# 345786) | CD16 (# 561304) |

Handling Protocol:
Labeling of the FACS tubes (e.g. round-bottom tubes, 1000×5 ml from BD, #352008); addition of the relevant extracellular antibodies in a quantity according to the manufacturer's recommendation; addition of 100 µl of EDTA whole blood, mixing; 15 minutes incubation at room temperature and protected from light; addition of 100 µl of IntraPrep Reagent 1 per tube and immediate mixing; 15 minutes incubation at room temperature and protected from light; In parallel, now start with the co-incubation of the intracellular antibody with blocker peptide (30 minutes at room temperature); first washing; addition of 4 ml of Cell Wash (BD, #349524) at room temperature, centrifugation at 300 g (=1400 rpm) for 5 minutes, decant supernatant well; carefully resuspend the pellet bubble-free using pipette; addition of 100 µl of Intraprep Reagent 2 per tube, ! do not shake !; 5 minutes incubation at room temperature and protected from light, then shake briefly;
addition of the respective intracellular antibody according to the following operating scheme:

| Tube | FITC | PE | PerCP | APC |
| --- | --- | --- | --- | --- |
| 1 (FMO) | | | | |
| 2 (EDIM staining) | Apo10 (Tavartis) | TKTL1 (Tavartis) | | |
| 3 (Peptide blocking) | Apo10 (Tavartis) | | | |

Next, 20' minutes incubation at room temperature and protected from light; addition of 4 ml of Cell Wash (BD, #349524); centrifugation at 300 g (=1400 rpm) for 5 minutes; decant supernatant well; third washing; addition of 4 ml of Cell Wash (BD, #349524); centrifugation at 300 g (=1400 rpm) for 5 minutes; decant supernatant well; addition of 200 µl of Cell Wash (BD, #349524);

The preparations are now ready for measurements and assessments.

Implementation of the FACS Measurement

All samples were analyzed with a BD FACSCantoII (BD Biosciences, Heidelberg, Germany). For each sample at least 10,000 relevant measurement events were recorded. FITC, PE, PerCP and APC fluorescence signals were displayed as logarithmically intensified data. The analysis was performed using the BD FACSDiva software v6.1 (BD Biosciences, Heidelberg, Germany).

"Gating Strategy" for Identification of the Macrophages (FIG. 1):

In the first step, for identification of the monocytes (referred to here as 'monos'), all leukocytes are plotted both in terms of their granularity (SSC-A) and also in terms of their size (FSC-H) (see FIG. 1a).

Only the cells thus characterized are further tested for the presence of the6surface marker CD14. These include both the brightest (i.e. highly positive) cells—these correspond to the upper, oval point cloud—and also the intermediately bright (i.e. normal positive) cells. Around these brightest and intermediately bright cells, a region (referred to as CD14) for further characterization is positioned (see FIG. 1b).

This region is additionally further tested for the presence of the surface marker CD16. These include both the brightest (i.e. highly positive) cells—these correspond to the upper, oval point cloud—and also the intermediately bright (i.e. normal positive) cells. Around these brightest and intermediately bright cells, a region (referred to as CD16) for further characterization is likewise positioned (see FIG. 1c).

All cells identified both as 'monocyte' and also as 'CD14 positive' are further tested for the intracellular presence of the Apo10 antibody—in order to optimize the subjective cutoff estimation.

The macrophages which are contained in the regions "monocyte" and "CD14" thus bear the surface markers CD14 and CD16. The macrophages thus identified are then divided by the horizontally lying cutoff (separating line) into two populations: Apo10 negative below the cutoff and as Apo10 positive cells above the cutoff. As the result of the measurement, the (EDIM) value is shown as the relative quantity of CD14+/CD16+ positive macrophages (in percent) which contain Apo10 (in comparison to the total quantity of the CD14/CD16 positive macrophages).

The result of this 'epitope detection in monocytes/macrophages'(EDIM) measurement consists in the statement or display of the relative quantity (in percent) of CD14+/CD16+ positive macrophages which also contain Apo10 (i.e. are also Apo10 positive), in comparison to the total quantity of the CD14/CD16 positive macrophages.

Macrophages in which the intracellularly introduced antibody binds to epitope have a higher signal strength than the other macrophages and count as Apo10 positive cells.

Cutoff Determination (A) Statement of the problem of correct cutoff determination using patient blood in the "EDIM normal" test as the example.

In this preparation, two intracellular detection antibodies, namely Apo10 and TKTL1, are simultaneously used and tested as regards staining and signal emission.

The measurement results are shown in FIG. 2 (a) and FIG. 2 (b).

FIG. 2 (a) shows the result of the Apo10 (FITC) EDIM staining, i.e. of the antibody Apo10 (FITC) EDIM detection method:

In the right-hand picture segment, the macrophages are represented, and in the left-hand picture segment the monocytes not further interpreted here. The content of Apo10 positive macrophages, i.e. of macrophages which in the FITC measurement channel give a light signal (red signal points), lies at 16.7% above the horizontal cutoff (separation boundary).

FIG. 2 (b) shows the result of the TKTL1 (PE) EDIM staining, i.e. of the antibody TKTL1 (PE) EDIM detection method:

In the right-hand picture segment, the macrophages are represented, and in the left-hand picture segment the monocytes not further interpreted here. The content of prominent macrophages, i.e. of macrophages which in the PE measurement channel give a light signal (red signal points), lies at 17.2% above the horizontal cutoff (separation boundary).

It is found that the assignment and interpretation of the (specifically) positive/prominent macrophages, i.e. the positioning of the cutoff (the separation boundary) is very difficult owing to the many non-specific signals and only the practiced person skilled in the art with much experience succeeds. In practice, only this practiced person skilled in the art recognizes within the macrophage cloud very narrow regions in which the positive macrophages stand out against the negative and positions the cutoff there.

Hence for an improved standardization, a reliable estimation of the (non-specific) background would be useful in order thus to be able to position the cutoff (separating line between positive and negative macrophages) more simply, and more accurately.

A conventional FMO control was therefore firstly performed here.

FMO Control

In/with this FMO control, the intrinsic fluorescence of the cells is determined and in addition the emission of the dyes of the extracellular antibodies in the measurement channel of the dye which is used for the intracellular staining, namely by performing a measurement without the antibody for the intracellular staining. Thus if there was an FMO control, a measurement was performed with antibodies against CD14 and CD16, but not with Apo10 antibodies.

FIG. 3 shows the relationship between the measurement results of the "actual test preparations" and the measurement results of this FMO control:

FIG. 3 (a) shows the result of the Apo10 (FITC) single staining (i.e. of the antibody Apo10 (FITC) EDIM detection method without secondary antibody TKTL1): In the right-hand picture segment, the macrophages are represented, and in the left-hand picture segment the monocytes not further interpreted here. The proportion of Apo10 positive macrophages, i.e. of macrophages which give a light signal in the FITC measurement channel (red signal points), lies at 16.7% above the horizontal cutoff (separation boundary).

FIG. 3 (b) shows the result of the FMO control (without FITC antibody):

In the right-hand picture segment, the macrophages are represented, and in the left-hand picture segment the monocytes not further interpreted here. The proportion of macrophages above the cutoff is only 0.8%, and these lie clearly distanced from the unstained macrophage cloud. In this, the cutoff was transferred from the measurement (a) to the FMO control measurement.

Conclusion:

The FMO control is not suitable for the results to be used for the measurement with the antibody. In addition to the specific signals due to binding of the antibody to the specific structures to be detected, all cells show stronger signals towards FMO. This can be caused by antibodies which bind non-specifically or which persist in the cells after the washing procedure.

Consequently, the cutoff must optimally be positioned so that the cells in the cloud remain below the cutoff and the actually positive cells are set apart by the cutoff.

However it is precisely this optimal setting apart (cutoff positioning) that requires long-term experience in the field of flow cytometry and especially experience with each individual problem such as for example the detection of Apo10 or TKTL1 in macrophages. This feature has hitherto prevented the establishment of the approach in routine laboratories and/or involves the risk of false results being determined and thereby false findings generated.

(C) Parallel measurement with Apo10 antibody and Apo10 antibody which is blocked by the specific peptide.

In order to reduce the non-specific portion of the signals, a second measurement was performed with a control preparation according to the invention which was made up analogously to the actual test preparation with the same components in the same quantities as in this actual test preparation, and differs from this solely in that the antibody is blocked at its specific binding site by prior incubation with the specific peptide (epitope peptide of the target structure). This blocked antibody can no longer enter into specific binding, so that the signals measured in this control preparation result from non-specific binding or a residuum of the antibody in the cells (in spite of the washing procedure).

The actual measurement (i.e. the measured value(s) of the actual test preparation) can be reduced by this value and thereby corrected, since this measured value represents the value of the (all) non-specific signals.

Before the actual measurement was performed, the suitable (molar) concentration of the blocking peptide must be determined. For this, in the present example, increasing molar proportion excess (from 1-fold (1×) to 1000-fold (1000×) of this blocker peptide was added to the Apo10 antibody (1× to 1000× mole of the peptide relative to one mole of antibody) and its effect on the non-specific binding observed, with this effect being manifested in the lowering of the signals of the macrophage cloud.

The titration curve obtained is shown in graph form in FIG. 4: the increasing proportion of peptide excess is shown on the x axis, and the relative value of the prominent macrophages above the cutoff (in %) on the y axis. Here, the cutoff used as the basis in the EDIM Apo10 single staining with the non-inhibited Apo10 antibody was established by the operator on the basis of the optical distribution of the cells.

For the actual measurement, two control preparations, one with the 10-fold excess of blocker peptide and one with a 500-fold excess of blocker peptide, were used. The results of these measurements are shown in FIG. 5: while with a 10-fold excess of the peptide specific signals are discernible above the cutoff (FIG. 5, a), these disappear at 500-fold concentration (FIG. 5, b). This 500-fold molar excess of the blocker peptide in comparison to the Apo10 antibody is necessary in order to eliminate the specific Apo10 signals. The Apo10 staining with 500-fold peptide excess (blocked Apo10 antibody) thus represents a control whose signals are made up of the intrinsic fluorescence of the cells, non-specifically bound antibodies and antibodies persisting in the cells after the washing procedure and thus indicates the non-specific signals. By subtraction of this non-specific measurement result from the measurement result which was generated with the unblocked Apo10 antibody, the determination of the specific measurement signal is possible.

Conclusion:

With the method according to the invention, an assessment method, moreover an automatable assessment method, is available in which in each case a measurement with blocked antibody is subtracted from the measurement with unblocked antibody, in order thus to determine the specific measurement signals.

For this, a concentration of the peptide to suppress specific signals completely must be selected. All signals then still measurable arise through intrinsic fluorescence of the cells, through non-specific binding of the antibody (the constant region of the antibody) or through antibody that has remained in the cell, which have bound to no epitope. All these non-specific signals can be determined with the antibody whose binding sites are blocked for specific binding by means of the peptide and thus specific binding is no longer possible. The antibody blocked with the peptide thus represents the magnitude of the non-specific binding. The measurement signals with unblocked antibody are thus made up of non-specific and specific signals and are therefore higher overall than the measurement signals which are determined in an FMO control. Thus by subtraction of the non-specific signals (measurement with blocked antibody) from the measurement results which were generated with the unblocked antibody, the specific signals can be determined. The assessment can thus be effected fully automatically and assessors who perform the assessment on the basis of optical information are no longer necessary for this. For this, the raw data which are deposited in the software of a flow cytometer are used. These can then be transferred for example into Excel tables for the calculation, so that they are easy to process further. As a result, the raw data which were generated with the blocked antibody are compared and subtracted from the raw data which were generated with the unblocked antibody, as a result of which the subtraction of the non-specific signals from the overall signals is possible, and the specific signals can be determined.

Before the measurement is performed, for every antibody a suitable concentration for the blockade of the binding site must be determined by testing. The concentration is specific for the combination of antibody with binding site and blockade reagent. This means that possibly with another antibody or other cell types a different ratio of peptide and antibody must be used. This ratio must therefore be freshly determined for each test method.

EXAMPLE 6: PRINCIPLE OF DETECTION USING THE METHOD ACCORDING TO THE INVENTION IN FLOW CYTOMETRY WITH THE ANTIBODY 'APO10' ON BLOOD SAMPLES

The test preparations are prepared as described in example 5. The/each "actual" test preparation is incubated with the specifically detection-capable (unblocked) fluorescent dye-coupled Apo10 antibody, and the/each control preparation is incubated with the blocked (at its binding domain with the epitope peptide) (and thus no longer specifically detection-capable) fluorescent dye-coupled Apo10 antibody. An FMO control (i.e. a parallel preparation for the "actual" test preparation but in contrast to this completely without Apo10 antibody) was also prepared.

FIG. 6 A is the schematic representation of two cells which show an Apo10 signal of different strength when (if, as soon as) the unblocked Apo10 antibody onto which a fluorescent dye is coupled is used for the detection in the flow cytometer. The CD16 signal is plotted on the X axis, and the Apo10 signal on the Y axis.

In FIG. 6 B it is shown that after blockade of the binding domain of the Apo10 antibody with the target peptide in both cells the Apo10 signal is reduced and as a result of this both cells in the diagram (of the flow cytometry measured values) migrate downwards. However, the magnitude of the reduction in the Apo10 signal is different for the two cells. With the cell on the right, the reduction in the Apo10 signal is stronger—it can now been seen markedly lower in the diagram than the cell on the left. The difference in Apo10 signal strength with unblocked antibody and blocked antibody gives the magnitude of the specific signals which are generated on the basis of the specific binding of the Apo10 antibody. The more strongly the Apo10 signal after blocking of the antibody with the peptide declines, the higher is the proportion of the specific signal. Thus the arrow length gives the magnitude of the decline in the Apo10 signal after blocking of the antibody (see FIG. 7). This is the magnitude of the specific Apo10 signals.

FIG. 7 A is identical with FIG. 6 A. FIG. 7 B corresponds to FIG. 6 B with additional graphic representation of the magnitude of the reduction in the Apo10 signal with both cells. The magnitude of the decline in the Apo10 positive cells represents the magnitude of the reduction in the signal which is created by the blockade of the binding domain of the Apo10 antibody with peptide. The reduction in the Apo10 signal is stronger with the cell located on the right. The difference in Apo10 signal strength with unblocked antibody and blocked antibody is greater with the right-hand cell, so that there a greater magnitude of specific signal is present. Although the Apo10 signal strength in the left-hand cell is higher than in the right-hand one, the right-hand one at the same time has a higher proportion of specific Apo10 signal. The delta between the measurement with unblocked Apo10 antibody and blocked Apo10 antibody is given by the arrow length in the diagram and shows the magnitude of the specific Apo10 staining. The arrows thus give the magnitude of the lowering of the signal owing to the blockade of the antibody with the peptide. Through the blockade of the Apo10 antibody with the peptide, the magnitude of the specific binding can be determined. At the same time, thereby the cells can also be identified which have the highest proportion of specific Apo10 signal, independently of the strength of the overall signal. As a result, it is possible to identify cells which while they have a low Apo10 signal, in which this Apo10 signal is nonetheless more specific than in other cells with a stronger Apo10 signal.

FIG. 8 is the schematic representation of cells which were stained with CD14 and CD16 and were plotted on the x axis against CD16. ("Actual") test preparations and FMO controls were analyzed.

In FIG. 8 A, the cells of the FMO control (without addition of Apo10 antibody) are shown.

In FIG. 8 B, it is shown that by addition of the fluorescence labeled Apo10 antibody, Apo10 signals are detected. The Apo10 signal increases because of specific and non-specific signals in most to almost all cells, as a result of which these cells migrate upwards in the diagram—the cell cloud migrates upwards. In this case, the cells with very much Apo10 signal set themselves somewhat apart above the cloud. However, no separate individual cloud of Apo10 positive cells thereby arises above the original FMO cell cloud.

FIG. 9 shows how the cutoff is positioned in a diagram according to FIG. 8 (diagram of cells which were stained with CD14 and CD16 and are plotted on the X axis against the CD16).

In FIG. 9 A, the cells of the FMO control (without addition of Apo10 antibody) are shown.

The dashed line marks the cutoff above the FMO cell cloud.

In FIG. 9 B, the dashed line marks the separating line (cutoff) above the FMO cell cloud, which was transferred into the cell cloud with (or after or in the case of) the Apo10 staining. However, this separating line transferred from the FMO is no longer suitable, since the cell cloud has migrated upwards on account of specific and non-specific signals due to addition of the fluorescence labeled Apo10 antibody. The Apo10 signal rises on account of specific and non-specific signals in most to almost all cells, as a result of which the cells in the diagram migrate upwards—the cell cloud migrates upward. The cells with very much Apo10 signal set themselves somewhat apart above the cloud. However, no separate individual cloud of Apo10 positive cells thereby arises above the original FMO cell cloud, but on the basis of the narrowing or lower density of the cells in one region a separating line (solid line) is introduced on the basis of this optical difference, which should divide the Apo10 positive from Apo10 negative cells. However, this separating line lies at a markedly higher level than can be deduced on the basis of the FMO control. Herein, a cell which lies above the separating line is regarded as Apo10 positive. However, cells which markedly gain in signal through addition of the Apo10 antibody still do not always cross the solid separating line, and are thereby assessed as negative, although this can actually be Apo10 positive cells with specific Apo10 signal.

FIG. 10 is again the schematic representation of cells which were stained with CD14 and CD16 and were plotted on the X axis against the CD16. Cells which bear the Apo10 antigen are shown as a circle with a triangle inside (▲) Cells which bear the Apo10 antigen and are labeled by binding of the fluorescence labeled Apo10 antibody onto this antigen and which emit fluorescence signals corresponding (to this binding) are here each shown as a circle with a square inside (■).

In FIG. 10 A, the measured values of the FMO control (without addition of Apo10 antibody) are shown. Apo10 antigen positive cells (shown as circle with triangle) are present, but are not detected here (since no bound Apo10 antibody is present).

In FIG. 10 B, it is shown that by addition of the fluorescence labeled Apo10 antibody, both the Apo10 antigen-bearing cells are stained (as circle with square). The two circles with triangle (▲) shown here indicate the previous position of these two Apo10 antigen-bearing cells according to FIG. 10 A. Through the addition of the Apo10 antibody, the proportion of non-specific signals also rises, in fact in all or almost all cells. This can for example be specifically caused by the stickiness of the antibody. The Apo10 signal in the left-hand cell labeled with the square (■) rises due to addition of the Apo10 antibody less strongly than the Apo10 signal in the right-hand cell labeled with a square. Although the overall strength of the Apo10 signal is thus lower in the right-hand cell than in the left, the magnitude of the specific Apo10 signal in the right-hand cell is higher than in the cell shown on the left.

FIG. 11 shows how a cutoff is positioned in a diagram according to FIG. 10.

By addition of the fluorescence labeled Apo10 antibody, a different part of the total number of the cells thereby rises to a different extent—the cloud migrates upwards. A skilled person in the field of flow cytometry is able on the basis of the narrowing or lower density of the cells in one region to recognize a cell population in the upper region of the overall cloud of cells, which thus have a high Apo10 signal and set themselves somewhat apart from the rest of the cloud, but as a rule do not make up a separate cloud separated from the main cloud. On the basis of this, here it is only possible to recognize these optical differences (narrowing of the cloud, lower density in the transition from Apo10 negative to Apo10 positive cells) and to introduce a correct separating line here on the basis of the experience of an expert. This separating line lies at a markedly higher level than can be deduced on the basis of the FMO control. This is due to the rise of the whole cloud owing to a combination of non-specific and specific Apo10 signals. Here, a cell which lies above the separating line is regarded as Apo10 positive. However, cells which markedly gain in signal through addition of the Apo10 antibody but still do not cross the separating line, are nonetheless assessed as negative. This means that a cell is not assessed as Apo10 positive solely on the basis of the increase in the Apo10 signal, but on the basis of the increase, but above all on the basis of the signal strength. Hence only the cells with the strongest signal and thus the cells above the separating line (cutoff) are assessed as positive. The assessment is thus only possible by a person skilled in the art. Positive cells which do not migrate above the cutoff are assessed as negative, although they can be positive cells, and can thus falsify the result.

EXAMPLE 7: USE OF THE METHOD ACCORDING TO THE INVENTION IN AN IMMUNOHISTOCHEMICAL DETECTION METHOD WITH THE ANTIBODY 'APO10' ON TISSUE SECTIONS OF ORAL CAVITY CARCINOMA

The antibody 'Apo10' is a monoclonal IgG2a antibody which is directed against the Apo10 epitope of the DNaseX protein, which is present in increased quantity in certain tumor cells and which can therefore serve as an indicator for identification of these tumor cells.

The antibody 'Apo10' was generated by an immunization of rats with the DNaseX peptide of the amino acid sequence CASLTKKRLDKLELRTEPGF. This amino acid sequence represents amino acid position 187 to 206 of the DNaseX protein (deoxyribonuclease I-like 1) which consists of a total of 302 amino acids. The whole sequence of the DNaseX protein is available under accession number gbAAV38793.1.

The target epitope of the antibody Apo10 is this (that) peptide which in its generation was used for the immunization used of the antibody producing cells (in the rat), namely a peptide with the amino acid sequence CASLTKKRLD-KLELRTEPGF.

The "'Apo10' antibody analysis staining" is performed on formalin-fixed and paraffin-embedded (FFPE) human tissue samples as so-called immunohistochemical (IHC) "Apo10 single staining" in combination with the labeled streptavidin biotin method (LSAB system).

In this, the FFPE tissue sections are first deparaffinized and rehydrated, heat-induced demasked, washed and optionally blocked with peroxidase and/or biotin and/or serum. This is followed by incubation with the detection antibody Apo10 as primary antibody dilution medium (e.g. application of 100 µl of primary antibody solution per tissue section), preferably overnight at 4° C. in a humidity chamber. The blocking of the binding domain is effected by incubation at 4° C. overnight with the 10-fold molar excess of the peptide compared to the antibody used, in order thus to obtain the primary antibody solution of the blocked antibody.

Following this, the tissue sections are washed (e.g. 2×2 minutes with washing buffer) and incubated with biotinylated secondary antibody (e.g. biotin-conj. F(ab')2 fragments donkey anti-rat IgG (H+L), dilution 1:100) for 45 mins at room temperature in a humidity chamber. After this, the tissue sections are again washed (e.g. 2×2 minutes with washing buffer) and incubated with HRP-conjugated streptavidin (e.g. LSAB™2 kit "LABEL") for 30 mins at room temperature in a humidity chamber.

A washing (e.g. 2×2 minutes with washing buffer) again follows and then an incubation with chromogen for HRP (e.g. Biogenex, DAB) for 5-10 minutes at room temperature in a humidity chamber (incubation time according to manufacturer's instructions). Next they are firstly stained with DAB and then a core staining performed with hematoxylin (e.g. 3 minutes at room temperature, depending on the desired intensity).

The staining is ended by washing or rinsing e.g. with tap water and finally the tissue sections mounted (e.g. in aqueous medium or after dehydration with a rising alcohol series/xylene in durable polymer medium).

The mounted tissue sections are analyzed and assessed by fluorescence microscopy.

The results of this analysis are shown in FIG. 12. They show that the Apo10 antibody detects the Apo10 epitope of the DNaseX protein in the cell nucleus of tumor cells (see FIG. 12 a). On the other hand, in stroma and healthy epithelial cells no Apo10 staining and hence no detection of the Apo10 protein epitope is discernible (not shown). The Apo10 staining in the cell nucleus of the tumor cells is no longer visible when the target peptide/epitope peptide (with the amino acid sequence CASLTKKRLDKLELRTEPGF) is added in 10-fold molar excess to the Apo10 antibody before the staining (see FIG. 12 b).

Comparative Immunohistochemical Measurement

For the comparison of two immunohistochemical measurements, in which immunohistochemical staining with unblocked antibody is compared with the staining with blocked antibody, consecutive sections, that is two successive sections of the (tumor) tissue, can be used. Thus by subtraction of the signals which were generated on two successive tissue sections the specific signals can be calculated. This method of consecutive sections was used in the case of FIG. 12.

Another possibility for the comparative measurement of immunohistochemical stainings consists in first adding the blocked antibody to the tissue section in order to detect the non-specific signals. After this, the same tissue section can be stained with the unblocked antibody in order to detect the signal which is generated by the specific binding between unblocked antibody and target epitope. As a result, the specific signals can be calculated by subtraction of the signals which were generated on the same tissue section. In this, the newly arising signals (signals from the second staining) represent the specific signals which are generated by the unblocked antibody. One modification of this form of consecutive staining consists in adding the blocked antibody in a different ratio compared to the following measurement with the unblocked antibody, so that for example the blocked antibody is used in 2-fold molar excess compared to the unblocked antibody. The excess of the blocked antibody can be raised still further, e.g. 3:1 ratio of blocked antibody in the first staining and unblocked antibody in the second staining. This ratio can be further raised to ratios of 200:1 or 500:1 or still higher. With this titration series, an optimal ratio between blocked antibody in the one measurement and unblocked antibody in the other measurement can be found, so that the strength of the specific signals can be selected such that these are sufficiently high. As a result, the specificity can be further raised, since the non-specific binding becomes ever more saturated and in a comparison with the unblocked antibody the specific binding can be determined still more selectively.

A further possibility for the comparative measurement of immunohistochemical stainings consists in first adding the blocked antibody to the tissue section in order to detected the non-specific signals. After this, the blocked antibody can be removed from the tissue section by gentle washing. The same tissue section is then stained afresh with the unblocked antibody. As a result, both specific and also the non-specific signals are detected. Through the subtraction (differencing) of the signals of the two measurements which were generated on the same tissue section, the specific signals can be calculated.

The invention claimed is:

1. A method of identifying, quantifying or discriminating specific signals from non-specific signals in a flow cytometry detection method comprising
    (a) providing (i) at least one test sample and (ii) at least one control sample, wherein the control sample comprises the same predetermined components and in the same quantities as the test sample,
    (b) contacting, in parallel, (i) the at least one test sample with at least one detector to form a test preparation, and (ii) the at least one control sample with at least one detector to form a control preparation,
    wherein the detector in each of the test preparation and control preparation comprises a binding domain, wherein the binding domain of the detector binds to and identifies specific target structures in the test preparation, wherein the binding domain of the detector in the control preparation is blocked, wherein the detector submits or generates a signal when bound to the specific target structures in the test preparation;

(c) differentially measuring (i) the signals in the at least one test preparation and (ii) the signals in the at least one control preparation, wherein differential measurement is conducted using flow cytometry; and (d) subtracting the measured signals in the at least one control preparation from the measured signals in the at least one test preparation, wherein the difference of the signals measured between the at least one control preparation and the at least one test preparation identifies, quantifies or discriminates specific signals of the one or more detectors in the test preparation from non-specific signals.

2. The method of claim 1, wherein the at least one detector comprises a detectable label.

3. The method of claim 2, wherein the detectable label becomes detectable upon the detector binding to a target structure.

4. The method of claim 1, wherein binding of the at least one detector to the at least one test sample or the at least one control sample emits a detectable signal.

5. The method of claim 1, wherein in step (b), the at least one test sample and the at least one control sample are contacted with the at least one detector in parallel.

6. The method of claim 1, wherein the at least one detector binds to a cell structure.

7. The method of claim 1, wherein the blocked binding domain of the detector in the control preparation is blocked with a structure which resembles the target structure.

8. The method of claim 1, wherein the one or more detectors is an antibody.

9. The method of claim 8, wherein the binding domain of the antibody incubated with the control preparation is blocked with a peptide which has the amino acid sequence of the target structure.

10. The method of claim 8, wherein the binding domain of the antibody incubated with the control preparation is blocked with a protein fragment or a protein which includes the target structure.

11. The method of claim 8, wherein the binding domain of the antibody incubated with the control preparation is blocked by binding with one or more peptide competitors, protein fragments, proteins, or combinations thereof, wherein each peptide competitor is similar in function and action to the peptide which has the amino acid sequence of the target structure, and each protein fragment or protein competitor includes the target structure.

12. The method of claim 8, wherein the antibody is a monoclonal antibody.

13. The method of claim 1, wherein the measuring of the binding in the control preparation and test preparation or the subtraction and difference display is effected partly automatically or fully automatically.

14. The method of claim 1, wherein the differential measurement further comprises an immunohistochemical test, wherein the detection of the signals in the control preparation and the test preparation is effected digitally, and the subtraction is effected partly automatically or fully automatically, and the difference display is effected digitally.

15. The method of claim 1, wherein the differential measurement further comprises an immunofluorescence test, wherein the detection of the signals in the control preparation and the test preparation is effected digitally, and the subtraction is effected partly automatically or fully automatically, and the difference display is effected digitally.

16. The method of claim 1, wherein the differential measurement of the binding further comprises a fluorescence microscopy test method.

17. The method of claim 1, wherein the measuring of the binding comprises a combination of flow cytometry and fluorescence microscopy test methods.

* * * * *